United States Patent [19]

Undheim et al.

[11] Patent Number: 5,610,141
[45] Date of Patent: Mar. 11, 1997

[54] DOUBLE CHAIN PEPTIDE COMPOUNDS HAVING HEMOREGULATORY ACTIVITY

[75] Inventors: Kjell Undheim, Sandvika; Magne Solbakken; Erik Agner, both of Oslo, all of Norway; Peter Kremminger, Linz, Austria; Meinolf Lange, Oslo, Norway

[73] Assignee: Nycomed Imaging AS, Norway

[21] Appl. No.: 362,411

[22] PCT Filed: Jun. 2, 1993

[86] PCT No.: PCT/GB93/01171

§ 371 Date: Nov. 30, 1994

§ 102(e) Date: Nov. 30, 1994

[87] PCT Pub. No.: WO93/24523

PCT Pub. Date: Dec. 9, 1993

[30] Foreign Application Priority Data

| Jun. 2, 1992 | [GB] | United Kingdom | 9211674 |
| Jun. 2, 1992 | [GB] | United Kingdom | 9211675 |
| Jun. 2, 1992 | [GB] | United Kingdom | 9211676 |

[51] Int. Cl.$^6$ ................................................ A61K 38/00
[52] U.S. Cl. ................ 514/15; 514/12; 514/13; 514/14; 514/16; 514/17; 514/18; 530/324; 530/326; 530/327; 530/328; 530/329; 530/330
[58] Field of Search ................ 530/324, 326, 530/327, 328, 329, 330; 514/12, 13, 14, 15, 16, 17, 18

[56] References Cited

U.S. PATENT DOCUMENTS

4,058,512  11/1977  Sievertsson et al. .

FOREIGN PATENT DOCUMENTS

0267741  5/1988  European Pat. Off. .
0408371  1/1991  European Pat. Off. .

OTHER PUBLICATIONS

Bold et al., *Helvetica Chimica Acta*, vol. 75, No. 3, 6 May 1992, Basel, Switzerland, 865–882.

Merck Manual, Fifteenth Ed., Merck & Co., Rahway, NJ (1987). see pp. 1120–1121.

*Primary Examiner*—Christine M. Nucker
*Assistant Examiner*—Benet Prickril
*Attorney, Agent, or Firm*—Bacon & Thomas

[57] ABSTRACT

Dipeptide compounds are disclosed, the two peptide chains being joined together at a C$\alpha$-atom of a non-terminal amino acid by a divalent bridging group —A—. The C$\alpha$-atoms joined to group —A— are located in equivalent positions in each peptide and each lack their native $\alpha$-side chain. The bridged dipeptide compounds disclosed have a stimulating activity on cell division, especially for myelopoietic and bone marrow cells.

11 Claims, No Drawings

DOUBLE CHAIN PEPTIDE COMPOUNDS HAVING HEMOREGULATORY ACTIVITY

The present invention relates to the use of peptides having a stimulating effect on cell proliferation, and to novel peptides having specific and/or general cell stimulating effects.

The mammalian body contains cells having enormously diverse structures and functions, and the mechanisms of differentiation and development have been the focus of much study. It is known that for systems of cells having a continuous turnover the mechanism commonly involves a reservoir of pluripotent stem cells which divide and constantly supply new cells to the system. While initially homogeneous the stem cells supplied from the "reservoir" soon become committed to one or other morphology and subsequently develop into the required functional cells.

Examples of such stem cell systems are the haemopoietic system in bone marrow and the epithelial and epidermal systems.

The manipulation or control of stem cell division is of great potential therapeutically and much research continues to be devoted to elucidating the mechanisms involved and the chemical messengers responsible. To date several biomolecules have been identified as possessing a role in cell production and differentiation either by the stimulation or inhibition of a step within the process. Myelopoiesis has been particularly well studied in this regard and molecules involved in its control include: colony-stimulating factors (CSF) such as granulocyte colony-stimulating factor (G-CSF), macrophage colony-stimulating factor (M-CSF), granulocyte-macrophage colony-stimulating factor (GM-CSF), multi-lineage colony-stimulating factor (multi-CSF; IL-3) [see Metcalf, Science 229: 16 (1985)], interleukin 11 (IL-11) [see Paul et al Proc Natl Acad Sci USA 87: 7521 (1990)], Lactoferrin [see Broxmeyer et al Blood Cells 11: 429 (1986)], prostoglandins [see Pelus et al J. Immunol 140: 479 (1988)], acidic (H-subunit) ferritin [see Broxmeyer et al Blood 68: 1257 (1986)], interferons ($\alpha$, $\beta$ and $\gamma$) [see Pelus et al supra. and Broxmeyer et al J. Immunol 131: 1300 (1983)], tumour necosis factors ($\alpha$ and $\beta$) [see Broxmeyer et al J Immunol 136: 4487 (1986)], transforming growth factor-$\beta$ [see Ottman et al J Immunol 140: 2661 (1988)], and activin and inhibin [see Broxmeyer et al Proc Natl Acad Sci USA 86: 779 (1989)].

It has also been found that the haemoregulatory pentapeptide (pEEDCK) inhibits the proliferation of myelopoietic cells selectively [see Paukovits et al Z. Naturforsch 37: 1297 (1982)] and other peptides corresponding to a narrow general formula were discovered to exert a similar inhibitory effect in hemopoiesis [see EP-A-112656 and WO90/02753]. Oxidation of the peptide monomers resulted in dimeric molecules linked by a cysteine bridge and these dimeric molecules were found to stimulate myelopoiesis [see Laerum et al. Exp. Hematol 16: 274 (1988)]. The (pEEDCK)$_2$ dimer and other similar compounds are disclosed in WO-A-88/03535. Further dimeric peptide compounds are disclosed in EP-A-408371 in which the disulphide bond has been replaced by a carbon or carbon/sulphur bridge linking the selected peptide chains. The bridge is thus relatively stable to hydrolysis but is itself inert and incapable of participating in receptor-dimer interactions.

Whilst we do not wish to be bound by theoretical considerations, it is presently believed that such peptide compounds interact with stromal cells in vivo and that the stromal cells are responsible for stimulating or inhibiting cellular division via other soluble factors. The dimers are thus believed to induce or promote stromatic production of stimulatory cellular regulatory factor(s) whilst the monomeric peptides may either inhibit that process or cause the production of factors which prevent or hinder cell division. Thus, according to current thinking, the stromal cells may act to amplify the stimulatory or inhibitory effects of the dimeric and monomeric peptides respectively.

There is a continuing need for dimeric peptide compounds capable of stimulating cell proliferation to a useful level in vivo. In this regard it should be noted that different degrees of stimulation may be more appropriate to certain clinical situations than to others and, in particular, selective stimulation of individual cell types is important.

The present invention provides a peptide compound comprising two single-chain hemoregulatory, especially haemopoesis-inhibiting, peptides joined together at the C$\alpha$ atoms of non-terminal amino acids in equivalent positions in each of said peptides via a carbon-carbon bond or via a terminally attached divalent bridging group —A—, the native $\alpha$-side chain being absent from said C$\alpha$ atoms, where A is a C$_{1-6}$ carbon chain which is a) mono- or poly-substituted by a group —R$^A$, —OR$^A$, —SR$^A$, —NR$^A$R$^A$ or —COOR$^A$ or by a halogen atom such as fluorine, chlorine, bromine or iodine (where each R$^A$ independently represents a hydrogen atom or a C$_{1-6}$-alkyl, -alkanoyl or -alkoxyalkyl group which may be mono- or poly-hydroxylated) and/or b) interrupted by one or more double or triple carbon-carbon bonds and/or c) interrupted by one or more groups —Z—, where each —Z— is independently —O—, —CO—, >C=NR$^8$ or —NR$^8$— (where each R$^8$ is independently a hydrogen atom or a C$_{1-6}$ alkyl or C$_{6-10}$ aryl group) or where one or more substituents or unsaturated carbon-carbon bonds are present in —A—, —Z— may also be —S— or ii) (CH$_2$)$_y$ where y is 1, 5 or 6, The total number of carbon atoms in the bridging group —A— is preferably not greater than 6.

Where group R$^A$ represents an alkyl, alkoxy or alkanoyl group, these may each be straight-chained or branched. Suitable alkyl groups include methyl, ethyl, 2-hydroxyethyl, propyl, butyl, 1,3-dihydroxybutyl, 2-methyl-3-hydroxybutyl and pentyl. Methoxy, ethoxy, propoxy and 2-hydroxypropoxy are all suitable alkoxy groups for group R$^A$, whilst the alkanoyl group may be formyl, acetyl, propionyl, for example.

For R$^8$ as an alkyl group, the alkyl carbon chain may be straight or branched and those groups mentioned above for R$^A$ are also suitable here.

Thus, suitable backbone structures of group A (which may be further substituted as set out above) include:

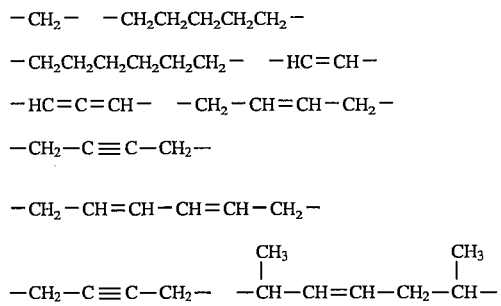

-continued

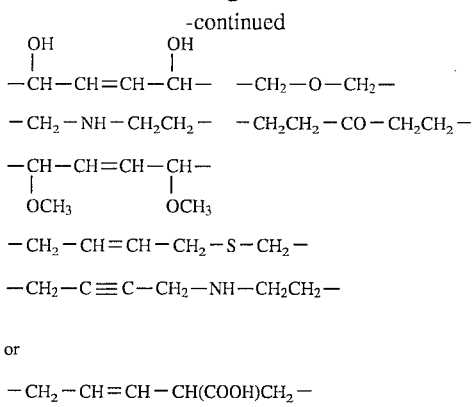

or

—CH₂—CH=CH—CH(COOH)CH₂—

Any single chain peptide which exhibits a hemoregulatory effect is suitable as the peptide which is bridged in accordance with the invention.

Alternatively expressed, the invention provides compounds according to the invention in which the said hemoregulatory peptide chains include those of formula:

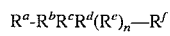 (I)

wherein $R^a$ represents

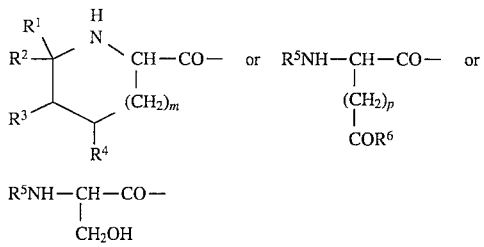

$R^b$ represents

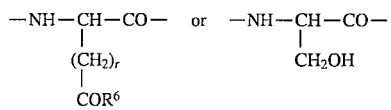

$R^c$ represents

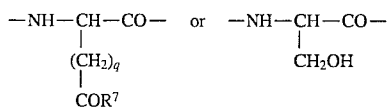

$R^d$ represents

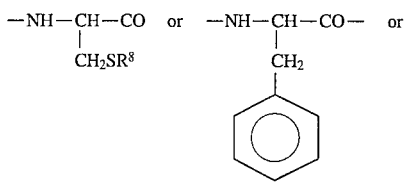

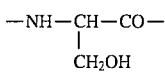

$R^e$ represents

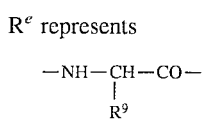

$R^f$ represents

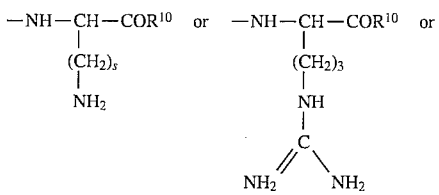

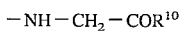

(wherein n and m independently represent 0 or 1;
p, q and r independently represent 1 or 2;
s represents 3 or 4;
$R^1$ and $R^2$ are both hydrogen atoms or together represent an oxo group;
$R^3$ and $R^4$ are both hydrogen atoms or together represent a carbon-carbon bond;
$R^5$ is hydrogen or an acyl group;
each $R^6$ and $R^7$ independently represent a hydroxy group or an amino group, but are preferably hydroxy groups,
$R^8$ represents hydrogen; a $C_{2-6}$ alkyl group; a $C_{7-20}$ aralkyl group, which may carry one or more hydroxy, amino or methoxy substituents; or a metabolically labile S-protecting group;
$R^9$ represents hydrogen or a methyl group; and
$R^{10}$ represents a hydroxy or amino group, the residue of the amino acid glutamine or a peptide having an N-terminal glutamine unit).

All the said amino acid residues may be in either the D or the L form. The L-form of the amino acids is, however, preferred.

Where an N-terminal protecting group $R^5$ is present this may, as indicated above, be an acyl group having 1–20 carbon atoms, e.g. a lower alkanoyl group having 1–5 carbon atoms such as the acetyl group, or an aroyl or aralkanoyl group having 7 to 20 carbon atoms such as the benzoyl or phenylacetyl group.

$R^5$ may also be an acyl group derived from an amino acid or a peptide chain. In particular, $R^5$ may be an acyl group derived from serine or any of the peptides derived from the following amino acid sequence by removal of successive N-terminal amino acids: Lys-Ile-Ile-His-Glu-Asp-Gly-Tyr-Ser.

The terminal amino group of the overall peptide of formula (I) is preferably protected, e.g. by acylation with an alkanoyl, aralkanoyl or aroyl group.

Where $R^8$ is a $C_{2-6}$ alkyl group this may, for example, be an ethyl, butyl or hexyl group. When $R^8$ is an aralkyl group, this may conveniently be an arylmethyl group such as benzyl, diphenylmethyl or triphenylmethyl. Where $R^8$ is a metabolically labile group this may, for example, be an arylthio group having 5 to 10 carbon atoms, e.g. the pyridyl thio group, or an acyl group as defined above.

The compounds of the invention are preferably pentapeptides, that is n is preferably 0.

The cyclic groups in the $R^a$ residue are preferably five-membered, that is m is preferably 0.

Insofar as any of the peptides defined by formula I above are of low or negligible haemoregulatory activity, they may nevertheless be effective, in the bridge form according to the invention, in stimulating cell proliferation.

In dimeric peptides formed from peptide chains as described in formula I the bridging point of the chain is desirably at $R^d$.

Particularly preferred peptide compounds according to the present invention are those of formula II

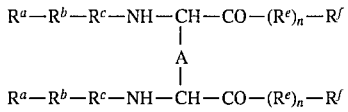

wherein $R^a$, $R^b$, $R^c$, $R^e$, $R^f$, A and n are all defined as above and the group —NH—CH—CO— is the derivatized form of $R^d$ which is attached to the bridging group —A— in such a manner that it's native side chain is absent.

One especially preferred peptide compound of formula II is

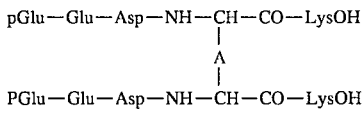

where group —A— is the divalent bridging group as discussed above.

The invention is of particular application in stimulating myelopoiesis in patients suffering from reduced myelopoietic activity, including bone marrow damage, agranulocytosis and aplastic anaemia. This includes treatment of patients having depressed bone marrow function due to immunosuppressive treatment to suppress tissue reactions, e.g. in bone marrow transplant surgery.

The compounds may also be used to promote more rapid regeneration of bone marrow after cytostatic chemotherapy and radiation therapy for neoplastic and viral diseases.

In addition, the new compounds may be of particular value where patients have serious infections due to lack of immune response following bone marrow failure.

Another clinical application will be in combination with the corresponding monomers or related myelopoiesis inhibitors as disclosed in EP-A-112656 or WO-A-90/02753 to induce alternating peaks of high and low activity in the bone marrow cells, thus augmenting the natural circadian rhythm of haemopoiesis. In this way, cytostatic therapy can be given at periods of low bone marrow activity, thus reducing the risk of bone marrow damage, while regeneration will be promoted by the succeeding peak of activity.

In general, in order to exert a stimulatory effect, the peptides of the invention may be administered to human patients orally or by injection in the dose range 0.001–100 mg, for example 1–5 mg, per 70 kg body weight per day. If administered intravenously or subcutaneously, the dose may be in the range 1–10 mg per 70 kg body weight per day, for example about 6 mg, for up to ten days. Nasal, topical (transdermal) or rectal administration is, of course, also feasible. In principle it is desirable to produce a concentration of the peptide of about $10^{-13}M$ to $10^{-5}M$ in the extracellular fluid of the patient.

According to a further feature of the present invention there are provided pharmaceutical compositions comprising as active ingredient one or more compounds of formula (I) as hereinbefore defined or physiologically compatible salts thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

The present invention thus provides the peptide compounds and compositions described above for use in the stimulation of cell division. Use of the peptide compounds according to the invention in the manufacture of a medicament to stimulate cell division forms a further aspect of this invention. Inhibition of myelopoiesis and bone marrow regeneration are of particular interest.

According to a still further feature of the present invention there is provided a method of stimulation of cell division, especially myelopoiesis which comprises administering an effective amount of a compound or a pharmaceutical composition as hereinbefore defined to a subject.

A further major use of the new peptides, however, is in the production of material for immunological assay techniques. The peptide may then be covalently attached to a suitable high molecular carrier such as albumin, polylysine or polyproline in order to be injected into antibody-producing animals (e.g. rabbits, guinea pigs or goats). In vitro immunisation techniques may also be used. High specificity antisera are obtained by use of well known absorption techniques, using the high molecular carrier. By introducing radioactivity ($^3$H, $^{125}$I, $^{14}$C, $^{35}$S) into the peptide molecule, a radioimmuno assay can be designed and used for determining the peptide in the different biological fluids such as serum (plasma), urine and cerebrospinal fluid.

The peptides of the invention may be synthesised in any convenient way. Suitable methods for forming the amino acid units are described in, for example, "Synthesis of Optically Active α-Amino Acids" by Robert M. Williams (Pergamon Press, 1989). In general, the reactive side chain groups present (amino, thiol and/or carboxyl) will be protected during the coupling reactions of the overall synthesis but it is possible to leave some side chain groups unprotected (hydroxy groups, imidazole groups, primary amide groups, amide groups in cyclic amino acids like pyroGlu) during the entire synthetic procedure.

The final step will thus be the deprotection of a fully protected or a partly protected derivative of a peptide of the general formula I and such processes form a further aspect of the invention.

Schöllkopf et al have described the preparation of a variety of amino acids by the metallation and subsequent alkylation of bis-lactim ethers (see, for example, Tetrahedron 39: 2085 (1983) and Topics Curr Chem 109: 65 (1983)). An adaptation of this method has proved particularly useful for the preparation of the bridged amino acids which form the basis of the present invention. In particular, a bis-lactim ether derived from a valine-glycine dipeptide forms a useful starting compound for the bridging reaction which may be summarized as follows:

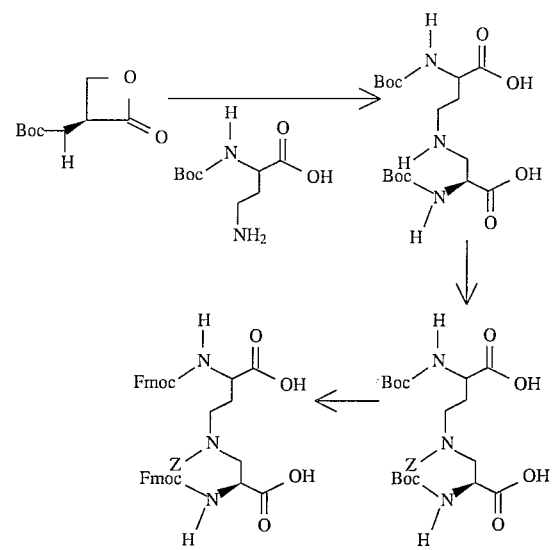

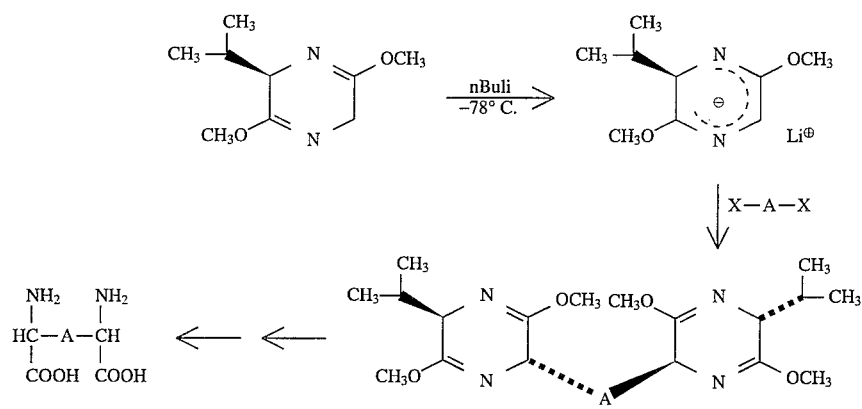

(wherein X is a leaving group such as halogen atom, for example bromine).

Bridged (S,S)-α,α'-diamino acids can be prepared by this method if D-valine is initially used to form the bis-lactim ether. Equally, bridged (R,R)-α,α'-diamino acids may be formed by the use of L-valine.

An alternative methodology useful for production of the bridge α,α'-diamino acids which form the basis of the bridged dipeptide compounds of the present invention is an adaptation of a method developed by Vederas et al., and reported in J. Am. Chem. Soc. 107: 7105 (1985) and J. Am. Chem. Soc. 110: 2237 (1988). This alternative methodology relies upon ring opening reactions of β-lactones derived from serine. The β-lactones may be reacted with a number of "soft" nucleophiles which cause cleavage of the lactone alkyl-oxygen bond. Aza-substituted bridged amino acids including oxa and thia analogues can be prepared by this methodology which is illustrated in the following scheme:

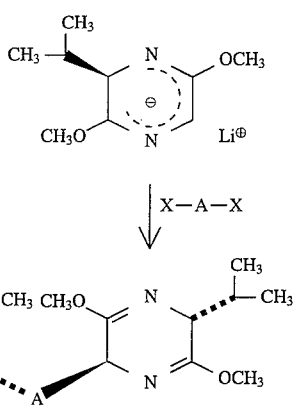

For bridged dipeptide compounds according to the invention wherein —A— is —CH$_2$—, reference may be had Belokon et al., in Izv. Akad. Nauk. SSSR. Ser Khim, (1987), 852 (Chemical Abstracts 108: 132255v).

Thus, the present invention also provides a process for producing a peptide compound comprising-deprotecting a partially or fully protected derivative thereof.

In another aspect, the invention further provides a process for producing a peptide compound, said process comprising
 a) metallating and subsequently alkylating a bis-lactim ether to form a bis-lactim dipeptide ether;
 b) hydrolysing a bis-lactim dipeptide ether of step (a) to form a bridged α,α'-diamino acid;
 c) introducing the remaining amino acids in the peptide chains; and
 d) deprotecting any protected group.

The bis-lactim dipeptide ethers and bridged acid α, α' diamino acid produced by this technique form a further aspect of the present invention.

Once the bridged dipeptide has been formed, then the remaining amino acids in the peptide chain can be introduced using conventional techniques.

In building up the peptide chains, one can in principle start either at the C-terminal or the N-terminal although only the C-terminal starting procedure is in common use.

Thus, one can start at the C-terminal by reaction of a suitably protected derivative of, for example lysine with a suitable protected derivative of cysteine. The lysine derivative will have a free α-amino group while the other reactant will have either a free or activated carboxyl group and a protected amino group. After coupling, the intermediate may be purified for example by chromatography, and then selectively N-deprotected to permit addition of a further N-protected and free or activated amino acid residue. This procedure is continued until the required amino acid sequence is completed.

Carboxylic acid activating substituents which may, for example, be employed include symmetrical or mixed anhydrides, or activated esters such as for example p-nitrophenyl ester, 2,4,5,trichlorophenylester, N-hydroxybenzotriazole ester (OBt), N-hydroxysuccinimidylester (OSu) or pentafluorophenylester (OPFP).

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline (EEDQ).

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start the C-terminal, for example by coupling N-protected lysine to the support.

A number of suitable solid phase techniques are described by Eric Atherton, Christopher J. Logan, and Robert C. Sheppard, J. Chem. Soc. Perkin I, 538–46 (1981); James P. Tam, Foe S. Tjoeng, and R. B, Merrifield J. Am. Chem. Soc. 102, 6117–27 (1980); James P. Tam, Richard D. Dimarchi and R. B. Merrifield Int. J. Peptide Protein Res 16 412–25 (1980); Manfred Mutter and Dieter Bellof, Helvetica Chimica Acta 67 2009–16 (1984).

It is also possible for the coupling reactions to be performed in solution.

A wide choice of protecting groups for amino acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag Stuttgart, N.Y., 1983; The Peptides, Analysis, synthesis, biology 1–7, Ed: Erhard Gross, Johannes Meienhofer, Academic Press, N.Y., San Fransisco, London; Solid phase peptide synthesis 2nd ed., John M. Stewart, Janis D. Young, Pierce Chemical Company.

Thus, for example amine protecting groups which may be employed include protecting groups such as carbobenzoxy (Z—), t-butoxycarbonyl (Boc-), 4-methoxy-2,3,6-trimethylbenzene sulphonyl (Mtr-), and 9-fluorenylmethoxycarbonyl (Fmoc-). It will be appreciated that when the peptide is built up from the C-terminal end, an amine protecting group will be present on the α-amino group of each new residue added and will need to be removed selectively prior to the next coupling step. For solid phase systems one particularly useful group for such temporary amine protection is the Fmoc group which can be removed selectively by treatment with piperidine in an organic solvent. For synthesis in solution, Boc- is a preferred protecting group, which can be introduced and removed in a conventional manner.

The amino acids or peptides often require to be silylated prior to protection eg. by addition of Fmoc in order to improve their solubility in organic solvents. Silylation and Fmoc protection reactions are summarized below:

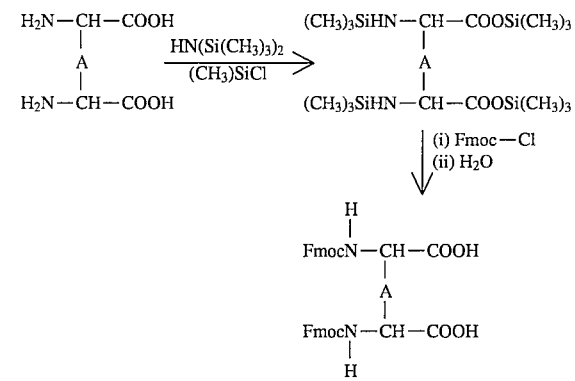

Carboxyl protecting groups which may, for example be employed include readily cleaved ester groups such as benzyl (—OBZl), p-nitrobenzyl (—ONB), or t-butyl (—tOBu) as well as the coupling on solid supports, for example methyl groups linked to polystyrene.

Thiol protecting groups include p-methoxybenzyl (Mob), trityl (Trt) and acetamidomethyl (Acm).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting groups prior to the next coupling step.

Amine protecting groups such as Boc and carboxyl protecting groups such as tOBu may be removed simultaneously by acid treatment, for example with trifluoro acetic acid. Thiol protecting groups such as Trt may be removed selectively using an oxidation agent such as iodine.

The cystein containing peptides may be synthesised by the methods described in the text with removal of all protecting groups including the thiol protecting groups as the last synthetic step.

The following Examples are given by way of illustration only.

EXAMPLE 1

(S,S)-2,7-Bis(9-fluorenylmethyloxycarbonylamino)-(E)-oct-4-ene-1,8-dioic acid a) 1,4-Bis((2R, 5S )-2,5-dihydro-3,6-dimethoxy-2-isopropyl-5-pyrazinyl)-(E)-but-2-ene To a stirred solution of (2R)-2,5-dihydro-3,6-dimethoxy-isopropylpyrazine (5.53 g, 30 mmol) in THF (100 ml) at −78° C., a 1.55M solution of butyllithium (19.62 ml, 31 mmol) in hexane was added by a syringe and stirring was continued for 1 hour at −78° C. Then a solution of (E)-1,4-dibromobut-2-ene (3.21 g; 15 mmol) in THF (20 ml) was added and stirring was continued overnight. The solvent was removed under reduced pressure and the residue was dissolved in diethyl ether and extracted with water. The organic layer was dried over magnesium sulfate, the ether was evaporated and the residue purified by flash chromatography (ethyl acetate/hexane 1/4; silica gel).

Yield 4.73 g (75%), pale yellow liquid.

$^1$H NMR (CDCl$_3$): δ0.67 (d, 6H), 1.04 (d, 6H), 2.1–2.4 (m,2H), 2.48 (dd,4H), 3.67 (s,6H), 3.68 (s,6H), 3.93 (dd, 2H), 4.03 (dd,2H), 5.35 (dd,2H).

$^{13}$C NMR (CDCl$_3$): δ16.52, 19.07, 31.65, 37.09, 52.16, 52.23, 55.62, 60.60, 127.50.

C$_{22}$H$_{35}$N$_4$O$_4$ (420) Calc: C: 62.86; H: 8.57 N: 13.33; Found: C: 62.65; H: 8.62 N: 12.91.

b) (S,S)-2,7-Diamino-(E)-oct-4-ene-1,8-dioic acid dimethyl ester

To a mixture of 1,4-bis((2R,5S)-2,5-dihydroxy-3,6-dimethoxy-2-isopropyl-5-pyrazinyl)-(E)-but-2-ene (4.02 g, 9.9 mmol) and 0.5 N HCl (40 ml, 20 mmol) 40 ml of dioxane were added, and the solution was stirred at ambient temperature for 4 hours. It was then extracted with diethyl ether, and aqueous ammonia added to the aqueous solution until pH 9 was reached. The aqueous phase was then extracted with chloroform and the organic layer was dried over magnesium sulfate. After removal of the solvent the valine methyl ester was removed by bulb-to-bulb distillation at 30°–40° C. (0.04 mbar). The undistilled title compound was used without further purification.

Yield 1.92 g (84.3%); yellow oil.

$^1$H NMR (CDCl$_3$): δ1.70 (s,4H), 2.20–2.60 (m,4H), 3.51 (dd,2H), 3.69 (s,6H), 5.46 (dd,2H).

$^{13}$C NMR (CDCl$_3$): δ37.99, 52.00, 54.11, 128.84, 175.32.

c) (S, S)-2,7-Diamino-(E)-oct-4-ene-1,8-dioic acid dihydrochloride (S,S)-2,7-Diamino-(E)-oct-4-ene-1,8-dioic acid dimethyl ester (1.65 g, 7.17 mmol) was heated under reflux with 6H HCl (10 ml, 60 mmol) for 2 hours. The solvent was then evaporated, the residue was dissolved in water (10 ml) and ethanol was added (100 ml). The white crystals were filtered off and dried in vacuum at 40° C.

Yield 1.32 g (67%); white crystals.

$^1$H NMR (D$_2$O): δ2.53 (dd,4H), 3.93 (dd,2H), 5.49 (dd, 2H).

$^{13}$C NMR (D$_2$O): δ33.57, 53.07, 128.49, 171.49

C$_8$H$_{16}$N$_2$O$_4$Cl$_2$ (275) Calc: C: 34.91; H: 5.81; N: 10.18; Cl: 25.78, Found: C: 36.58; H: 5.80; N: 9.70; Cl: 26.01.

FAB-MS signal at m/z 405.3(11), 203.2(100), 157.1(19), 130.1(7), 93.0(18), 73.9(13).

d) (S,S)-2,7-Bis(9-fluorenylmethyloxycarbonylamino)-(E)-oct-4-ene-1,8-dioic acid The acid hydrochloride (S,S)-2,7-Diamino-E-oct-4-ene-1,8-dioic acid dihydrochloride (1.59 g, 5.8 mmol) was suspended in hexamethyldisilazane (20 ml) and 1 ml of trimethylsilyl chloride was added. Then the suspension was refluxed overnight. The solvent was removed under reduced pressure and the residue was dissolved in anhydrous methylene chloride. This solution was cooled to 0° C. and a solution of 9-fluorenylmethyl chloroformate (3.10 g, 12 mmol) in methylene chloride was added. The solution was stirred for 1 hour before the cooling bath was removed. The next morning the solvent was evaporated and the residue was dissolved in THF. Then the mixture was quenched with 1N aqueous HCl and the solution was stirred for two hours.

The organic solvent was removed and the water phase was extracted with chloroform. The organic layer was dried over magnesium sulfate and evaporated. The residue was dissolved in methylene chloride and precipitated with ether.

Yield 2.50 g (67%); white crystals.

$^1$H NMR (DMSO): δ2.2–2.4 (s,4H), 3.6 (s,2H), 3.9–4.5 (m,8H), 5.55 (s,2H), 7.2–8.1 (m,16H).

$^{13}$C NMR (DMSO): δ33.98, 46.56, 53.93, 65.49, 119.66, 124.81, 126.61, 127.17, 127.98, 140.19, 143.28, 155.43, 172.59.

C$_{38}$H$_{34}$N$_2$O$_8$(646) Calc: C: 70.59; H: 5.26; N: 4.33, Found: C: 70.17; H: 5.58; N: 4.08.

FAB-MS signal at m/z 661.3(3), 647.4(3), 191.2(17), 179.2(100), 165.1(18), 78.9(31).

EXAMPLE 2

(S,S)-2,7-Bis(9-fluorenylmethyloxycarbonylamino)-(Z)-oct-4-ene-1,8-dioic acid a) 1,4-Bis((2R,5S)-2,5-dihydro-3,6-dimethoxy-2-isopropyl-5-pyrazinyl)-(Z)-but-2-ene (2R)-(−)-2,5-Dihydro-3,6-dimethoxy-2-isopropylpyrazine (1.3 ml, 6.4 mmol) was dissolved in dry THF (20 ml), and cooled to -78° C. BuLi (1.6M in hexane, 3.9 ml, 6.4 mmol) was added dropwise, and the solution was stirred for 30 minutes. Cis-1,4-dichloro-2-butene (0.32 ml, 3 mmol) was dissolved in dry THF (10 ml), and added in one batch at −78° C. The reaction mixture was stirred overnight under N$_2$ atmosphere. The reaction was quenched with ammonium chloride (3 ml), and evaporated. The residue was extracted with diethyl ether, and the organic phase was washed twice with water. Then it was dried over MgSO$_4$, and evaporated. Purification was carried out on silica gel (heptane:EtOAc/ 2:1).

Yield: 0.81 g (60%), light yellow oil.

TLC (heptane:EtOAc/2:1): Rf=0.39

HPLC (50–100% MeOH, 10 minutes): Rt=6.75 minutes.

$^1$HNMR (CDCl$_3$): δ0.66 (d,6H), 1.02 (d,6H), 2.55 (m,2H), 2.66 (m,4H), 3.66 (s,6H), 3.70 (s,6H), 3.90 (t,2H), 4.01 (m,2H), 5.39 (t,2H).

b) (S,S)-2,7-Diamino-(Z)-oct-4-ene-1,8-dioic acid dimethylester 1,4-Bis((2R,5S)-2,5-dihydro-3,6-dimethoxy-2-isopropyl-5-pyrazinyl)-(Z)-but-2-ene (0.58 g, 1.23 mmol) was dissolved in dioxane (8 ml), and 0.25M HCl (8 ml, 2.5 mmol) was added and stirred overnight at ambient temperature. TLC(MeCN:MeOH:H$_2$O/4:1:1). The solution was extracted with diethyl ether, and the aqueous phase was evaporated. The residue was dissolved in a small amount of water, and aqueous ammonia solution was added until a pH of 9 was reached. The aqueous phase was extracted twice with diethyl ether, and the organic phase was dried over MgSO$_4$ and evaporated.

Yield: 0.6 g, yellow oil.

c) (S,S)-2,7-Diamino-(Z)-oct-4-ene-1,8-dioic acid dihydrochloride

To a mixture of (S,S)-2,7-diamino-(Z)-oct-4-ene-1,8-dioic acid dimethyl ester (0.6 g, 1.3 mmol), conc HCl (1 ml) and dioxane (10 ml) were added and the solution was refluxed for 2 hours, and then evaporated.

Yield: 0.6 g, white solid.

¹H NMR (D₂O): δ0.88 (2d,6H), 2.15 (m,1H), 2.57 (2d, 4H), 3.68 (m, 1H), 3.86 (m,2H), 5.51 (m, 2H).

d) (S,S)-2,7-Bis(9-fluorenylmethyloxycarbony-lamino)-(Z)-oct-4-ene-1,8-dioic acid The acid hydrochloride obtained from step (c) (0.6 g, 2.2 mmol) was suspended in hexamethyldisilazane (12 ml) and trimethylsilyl chloride (12 ml). The suspension was refluxed overnight under nitrogen. Excess HMDS and TMS-Cl were distilled off in vacuo. The residue was dissolved in dry methylchloride, and cooled to 0° C. A solution of fluorenylmethyl chloroformate (712 mg, 2.8 mmol) in dry methylchloride was added, the mixture was stirred for 2 hours, and then evaporated. The residue was dissolved in THF, quenched with 1M HCl, and stirred for 2 hours. The organic solvent was removed, and the aqueous phase was extracted with chloroform. The organic layer was dried over MgSO₄, and evaporated.

Purification was carried out on silica (heptane:EtOAc:AcOH/3:6:1).

HPLC (40–70% MeCN in 0.1% TFA, 10 minutes): Rt=4.75 minutes.

¹H NMR (CDCl₃): δ2.4–2.7 (s,4H), 3.7 (s,2H), 4.0–4.5 (m,8H), 5.5 (s,2H), 7.1–7.8 (m,16H).

EXAMPLE 3

(S,S)-2,7-Bis-(9-fluorenylmethyloxycarbony-lamino)-oct-4-yne-1,8-dioic acid a) 1,4-Bis((2R,5S)-2,5-dihydro-3,6-dimethoxy-2-isopropyl-5-pyrazinyl)-but-2-yne (2R)-(−)-2,5-Dihydro-3,6-dimethoxy-2-isopropylpyrazine 2.76 g (15mmol) was dissolved in 100 ml dry THF and cooled to -78° C., then 9.5 ml of a 1.6M solution BuLi (15 mmol) was added dropwise with stirring. After 1 hour 0.92 g (7.5 mmol) of 1,4-dichloro-2,3-butyne was introduced slowly. TLC and gas chromatography (GC) of the reaction mixture 1 hour later showed substantial amounts of unreacted 2,5-dihydro-3,6-dimethoxy-2-isopropylpyrazine and the monoalkylated product. The reaction was allowed to continue overnight and reach ambient temperature gradually. THF was evaporated off under reduced pressure and the residue partitioned between ether and water. The water phase was extracted twice with ether, dried (MgSO₄) and evaporated. Kugelrohr distillation of the reaction mixture to give 2.3g (77%) pure product.

¹H NMR (CDCl₃): δ4.03 (m, 4H, ring H's); 3.68 (m, 12H, 4 x OCH₃), 2.63 (br. AB q, 4H, 2 x CH₂), 2.27 (m, 2H, 2 x CH(CH₃)₂), 1.05 (d, J=6.8Hz, 6H, 2 x CH₃); 0.64 (d, J=6.8Hz, 6H, 2 x CH₃).

¹³C NMR (CDCl₃): δ163.9, 161.0, 77.4, 60.6 (60.68), 54.6 (54.2), 52.3, 52.2, 31.6 (31.20), 25.5 (25.6), 19.3 (19.5), 16.7 (16.9).

MS (CI) 419 (M⁺+, 55), 403 (4), 391 (7), 279 (15), 236 (17), 183 (44), 167 (34), 149 (100), 141 (41), 113 (44).

b) (S,S)-2,7-Diamino-oct-4-yne-1,8-dioic acid dimethyl ester

To the product from step (a) was added 20 ml 1.0M HCl and 60 ml of MeOH to give 0.25M HCl in H₂O/MeOH. The reaction mixture was stirred at ambient temperature overnight and, after determining that no starting material remained, all solvent was removed. The residue was dissolved in water, extracted with ether and the water phase neutralized to pH 8 with conc. NH₄OH. The solution was washed with ether and extracted several times with EtOAc until all product had been taken up by the EtOAc phase. This was then dried, the solvent removed and the valine methyl ester separated from the mixture by Kugelrohr distillation to give 0.97 g (78%) of the methyl ester title compound.

¹H NMR (D₂O): δ4.0 (m, 2H, HC-α), 3.6 (d, 6H, 2 x OCH₃), 2.6(m, 4H, 2 x CH₂).

¹³C NMR (D₂O): δ171, 81.6, 61.6, 56.6, 20.5.

c) (S,S)-2,7-Diamino-oct-4-yne-1,8-dioic acid

Sufficient MeOH to dissolve the product from step (b) and 20 ml 6M HCl were mixed and stirred at ambient temperature overnight. TLC using 1:1:1:1/ nBuOH:EtOAc:MeOH:H₂O mixture and ninhydrin spray showed the presence of methyl ester. The reaction mixture was refluxed at 60° C. for 24 hours until all the methyl ester was hydrolysed. The solution was evaporated to dryness, the residue dried under high vacuum and used without further purification.

¹³C NMR (D₂O): δ172.3, 81.1, 55.0, 24.3.

d) (S,S)-2,7-Bis(9-fluorenylmethyloxycarbony-lamino)-oct-4-yne-1,8-dioic acid 50 ml of HMDS and 1 ml of TMSCl were added to the product from above and the mixture refluxed at 120° C. under nitrogen until a clear solution was obtained, after about 24 hours. Excess HMDS was then distilled off and the resulting product was dissolved in 50 ml dry CH₂Cl₂ and cooled to 0° C. 3g of FMOC-Cl dissolved in 20 ml dry CH₂Cl₂ was added gradually with stirring and the reaction was left overnight. The solvent was removed under reduced pressure and the product partitioned between saturated aqueous NaHCO₃ solution and ether to remove unreacted FMOC-Cl and other FMOC decomposition products. The aqueous solution was cooled to 0° C. and acidified with 2M HCl to pH 3 and the product extracted up to 5 times with EtOAc, then washed, dried and evaporated. Chromatography using CHCl₃:MeOH/96:4 gave 2.35g (66%) of the title comopund. Although TLC showed this to be pure, reverse phase HPLC showed the presence of impurities that almost coincided with the major product peak. The product in 40% MeCN with 0.1% TFA was purified by preparative HPLC, using a Beckman ODS C-18 column using 0.1% TFA in H₂O and then was 0.1% TFA in MeCN as eluant.

¹H NMR (DMSO): δ7.9 (d, J 7.3 Hz, 4H, arom. H), 7.7 (d, J=7 Hz, 4H, arom. H), 7.3 (d triplet, J 7.2 Hz, 8H, arom. H), 4.26 (m, 8H, OCH₂, 2 x CH), 2.5 (m, 4H, CH₂).

¹³C NMR (DMSO): δ170.4, 154.5, 142.5, 139.4, 126.5, 125.9, 124.2, 119.0, 77.6, 65.5, 53.0, 46.5, 21.7.

EXAMPLE 4

(S,S)-2,4-Bis(9-fluorenylmethyloxycarbonylamino)-(E)-pentane-1,5-dioic acid a) 1,1-Di((2R,5S)-2,5-dihydro-3,6-dimethoxy-2-isopropyl-5-pyrazinyl)-(E)-methane To a stirred solution of (2R)-2,5-dihydro-3,6-dimethoxy-isopropylpyrazine (5.53 g, 30 mmol) in THF (100 ml) at −78° C., a 1.55M solution of butyllithium (19.62 ml, 31 mmol) in hexane is added by a syringe and stirring is continued for 1 hour at −78° C. Then a solution of (E)- bromochloromethane (15 mmol) in THF (20 ml) is added and stirring is continued overnight. The solvent is removed under reduced pressure and the residue is dissolved in diethyl ether and extracted with water. The organic layer is dried over magnesium sulfate, the ether is evaporated and the residue purified by flash chromatography (ethyl acetate/hexane 1/4; silica gel).

b) (S,S)-2,4-Diamino-(E)-pentane-1,5-dioic acid dimethyl ester

To a mixture of 1,1-di((2R,5S)-2,5-dihydroxy-3,6-dimethoxy-2-isopropyl-5-pyrazinyl)-(E)-methane (4.02 g, 9.9 mmol) and 0.5 N HCl (40 ml, 20 mmol) 40 ml of dioxane are added, and the solution stirred at ambient temperature for 4 hours. It is then extracted with diethyl ether, and aqueous ammonia added to the aqueous solution until pH 9 is reached. The aqueous phase is then extracted with chloroform and the organic layer dried over magnesium sulfate. After removal of the solvent the valine methyl ester is removed by bulb-to-bulb distillation at 30°–40° C. (0.04 mbar). The undistilled title compound is used without further purification.

c) (S,S)-2,4-Diamino-(E)-pentane-1, 5-dioic acid dihydrochloride (S,S)-2,4-Diamino-(E)-pentane-1,5-dioic acid dimethyl ester (1.65 g, 7.17 mmol) is heated under reflux with 6N HCl (10 ml, 60 mmol) for 2 hours. The solvent is then evaporated, the residue is dissolved in water (10 ml) and ethanol is added (100 ml). The white crystals are filtered off and dried in vacuum at 40° C.

d) (S,S)-2,4-Bis(9-fluorenylmethyloxycarbonylamino)-(E)-pentane-1,5-dioic acid The acid hydrochloride (S,S)-2,4-diamino-(E)-pentane-1, 5-dioic acid dihydrochloride (1.59 g, 5.8 mmol) is suspended in hexamethyldisilazane (20 ml) and 1 ml of trimethylsilyl chloride is added. Then the suspension is refluxed overnight. The solvent is removed under reduced pressure and the residue is dissolved in anhydrous methylene chloride. This solution is cooled to 0° C. and a solution of 9-fluorenylmethyl chloroformate (3.10 g, 12 mmol) in methylene chloride added. The solution is stirred for 1 hour before the cooling bath is removed. The next morning the solvent is evaporated and the residue is dissolved in THF. Then the mixture is quenched with 1N aqueous HCl and the solution stirred for two hours. The organic solvent is removed and the water phase is extracted with chloroform. The organic layer is dried over magnesium sulfate and evaporated. The residue is dissolved in methylene chloride and precipitated with ether.

EXAMPLE 5

(S,S)-2,9-Diaminodecane dioic acid a) 1,6-Bis[(2R,5S)-3,6-dimethoxy-2-isopropyl-2,5-dihydro-5-pyrazinyl]hexane (R)-2,5-Dihydro-3,6-dimethoxy-2-isopropylpyrazine (4.12 g, 22.4 mmol) was dissolved in anhydrous THF and the solution was cooled to −78° C. A solution of BuLi in hexane (22.4 mmol, 14.0ml) was added. After 30 minutes at −78° C. a solution of 1,6-dibromohexane (11.2 mmol, 2.73g) in THF was added dropwise, and the solution came to ambient temperature overnight. After hydrolysis with phosphate buffer (pH=7) the mixture was extracted with diethyl ether, and the organic layer was washed with water and brine. After drying (MgSO$_4$) the solvent was evaporated and the residue was purified by flash chromatography (hexane/ethyl acetate 9/1).

Yield: 2.57g (51%).

$^1$H NMR(CDCl$_3$) δ: 0.67 (d,6H), 1.04 (d,6H), 1.10–1.30 (m,8H), 1.60–1.85 (m,4H), 2.15–2.35 (m,2H), 3.66 (s,6H), 3.67 (s,6H), 3.91 (dd,2H), 3.95–4.05 (m,2H). $^{13}$C NMR (CDCl$_3$) δ: 16.54, 19.08, 24.44, 29.46, 31.63, 34.15, 52.27, 52.28, 55.47, 60.68, 163.41, 163.96.

FAB-MS signals at m/z 451.2(80), 407.2(33), 141.0(100). C$_{24}$H$_{42}$N$_4$O$_4$ (450).

b) Dimethyl (S,S)-2,9-Diaminodecanedioate

A solution of 1,6-bis[(2R,5S)-3,6-dimethoxy-2-isopropyl-2,5-dihydro-5-pyrazinyl]-hexane (2.57 g, 5.71 mmol) in 40 ml dioxane and 22.8 mmol HCl (1.90 ml) in 36 ml water was stirred at ambient temperature for 6 hours, the solvent was removed, and the solution was extracted with diethyl ether. Aqueous ammonia solution was added until a pH of 9 was reached, and the solution was extracted with chloroform. The organic layer was dried (MgSO$_4$). The valine methyl ester was distilled under vacuum (0.03 torr, ambient temperature).

Yield: 1.48g (100%).

$^1$H NMR (CDCl$_3$) δ: 1.20–1.70 (m,16H), 3.36 (dd,2H), 3.65 (s,6H). $^{13}$C NMR (CDCl$_3$) δ: 25.40, 29.06, 34.77, 51.76, 54.30, 176.51.

c) (S,S)-2,9-Diaminodecanedioic acid.2HCl

Dimethyl (S,S)-2,9-diaminodecanedioate (1.40g, 5.38 mmol) was dissolved in 6N HCl (40 ml, 240 mmol), and stirred under N$_2$ at 60° C. for 12 hours. The solvent was evaporated, the residue dissolved in EtOH and crystallized by the addition of diethyl ester. The crystals were filtered off.

Yield: 0.700 g, white crystals (42.7%).

$^1$H NMR (D$_2$O) δ: 1.07–1.37 (m, 8H), 1.60–1.90 (m, 4H), 3.85 (m,2H), $^{13}$C NMR (D$_2$O) δ: 23.81, 27.65, 29.61, 53.09, 172.55.

FAB-MS signals at m/z 439.3(15), 340.3(100), 233.2(11). C$_{10}$H$_{22}$N$_2$Cl$_2$O$_4$ (450): Calc: N, 9.18. Found: N, 9.13.

d) (S,S)-2,9-Bis(9-fluorenylmethyloxycarbonylamino)decanedioic acid (S,S)-2,6-Diaminodecanedioic acid dihydrochloride (0.50 g, 1.64 mmol) was suspended in HMDS and TMSCl and refluxed under nitrogen overnight. The solvents were removed and the residue was dissolved in anhydrous CH$_2$Cl$_2$. The solution was cooled to 0° C. and a solution of FmocCl (1.69g, 6.56 mmol) in CH$_2$Cl$_2$ added. The solution was stirred overnight, the solvent removed and the residue dissolved in THF. After addition of 5 ml 0.5M HCl the mixture was stirred for 2 hours, extracted with chloroform and dried (MgSO$_4$). The residue was purified by flash chromatography (heptane/ethyl acetate/acetic acid 4/6/1).

Yield: 0.580 g (52.5%).

$^1$H(DMSO) δ: 1.00–1.44(m,8H), 1.44–1.80(m,4H), 3.90(s,2H), 4.13–4.43(m,4H), 7.25–8.05(m,16H); $^{13}$C (DMSO) δ: 21.29, 25.63, 28.62, 31.08, 46.86, 54.17, 65.70, 120.25, 125.44, 127.20, 127.77, 140.86, 143.96, 144.04, 156.21, 174.28.

FAB-MS signal at m/z 699.5(6), 677.4(2), 603.6(4), 409.3(4), 339.3(4), 179.1(55), 72.9(100).

EXAMPLE 6

(S,S)-2,8-Diaminononanedioic acid a) 1,5-Bis[(2R,5S)-3,6-dimethoxy-2-isopropyl-2,5-dihydro-5-pyrazinyl]-pentane To a solution of (R)-2,5-dihydro-3,6-dimethoxy-2-isopropylpyrazine (3.68 g, 20 mmol) in THF (68 ml) a 1.6M solution of n-BuLi in hexane (12.8 ml, 20.4 mmol) was added dropwise (10 minutes) and stirring was continued at −78° C. for 1 hour. Then a solution of 1,5-dibromopentane (2.3 g, 10 mmol) in THF (13.2 ml) was added dropwise and the mixture was allowed to come to ambient temperature overnight. The reaction was quenched by addition of 50 ml of NaHCO$_3$ and the mixture was diluted with ether (50 ml) and water (20 ml). After separation the aqueous layer was extracted twice with ether (50 ml) and the combined organic layer was dried (MgSO$_4$), filtered, concentrated and purified by flash chromatography (silica gel, hexane: ethyl acetate= 12:1).

Yield 3.68 g (8.43 mmol, 84.3 %).

$^1$H-NMR (300 MHz, CDCl$_3$): δ4.02 (q, 2H, J 2.1 Hz), 3.92 (t, 2H, J 3.3 Hz), 3.68 (s, 12H), 2.28 (d sept, 2H, J 3.3, 6.8 Hz), 1.71 (m, 4H), 1.21 (m, 6H), 1.05 (d, 6H, J 6.8), 0.68 (d, 6H, J 6.8); $^{13}$C-NMR (75 MHz, CDCl$_3$): δ163.89, 163.31, 60.62, 55.40, 52.22, 52.19, 34.02, 34.56, 29.31, 24.33, 19.01, 16.48.

FAB-MS m/z 437 (M+1).

C$_{23}$H$_{40}$N$_4$O$_4$ (436.59) Calc: C, 63.28; H, 9.23; N, 12.83. Found: C, 62.95; H, 9.01; N, 12.91.

b) Dimethyl (S,S)-2,8-diaminononanedioate

The 1,5-bis[(1S,4R)-3,6-4-isopropyl-2,5-dihydropyrazinyl]-pentane (2.8 g, 6.4 mmol) was dissolved in dioxane (51.2 ml) and 0.5M HCl (51.2 ml) and stirred for 4 hours at ambient temperature. This mixture was washed with diethyl ether (100 ml), brought to pH 9 by addition of 25% ammonia in water, and quickly extracted with CHCl$_3$ (3×75 ml). The organic layer was dried with MgSO$_4$, filtered, and concentrated. The methyl valinate was removed by kugelrohr distillation (25°–50° C., 0.01 torr) to yield 1.505 g (0.11 mmol, 95.5%).

$^1$H NMR (300 MHz, CDCl$_3$): δ3.71 (s, 6H), 3.43 (t, 2 H, J 6.0 Hz), 1.70 (m, 2H), 1.57–1.34 (m, 8H); $^{13}$C NMR (75 MHz, CDCl$_3$): δ=176.40, 54.33, 51.86, 34.79, 29.08, 25.42.

c) (S,S)-2,8-Diaminononanedioic acid

The ester from step (b) was heated under reflux in 6M HCl (7.2 ml) for 2 hours under N$_2$. The volatile compounds were evaporated. The residue was dissolved in water (5 ml), ethanol was added (20 ml) and slow addition of ether led to a white, crystalline precipitate. This mixture was kept for 12 hours in the refrigerator, filtered, washed with ether and dried under vacuum.

Yield 1.37 g (4.71 mmol, 77.4%).

$^1$H NMR (300 MHz, CDCl$_3$): δ3.74 (m, 2H), 1.80–1.63 (m, 4H), 1.38–1.15 (m, 6H); $^{13}$C NMR (75 MHz, CDCl$_3$): δ173.35, 53.62, 29.71, 27.65, 23.65.

FAB-MS m/z (M$^+$−72).

C$_9$H$_{20}$Cl$_{12}$N$_2$O$_4$ (291.17). Calc: C, 37.13; H, 6.92. Found: C, 37.90; H, 7.21.

d) (S,S)-2,8-Bis(9-fluorenylmethyloxycarbonylamino)nonanedioic acid

A suspension of (S,S)-2,8-diaminononane diacid (291 mg, 1 mmol) in TMSCl (260 mg, 2.4 mmol) and HMDS (3.5 ml) was refluxed under N$_2$ overnight. After cooling to ambient temperature the volatile parts were removed (up to 50° C., 0.01 torr), the residue was dissolved in CH$_2$Cl$_2$ (6.6 ml), cooled to 0° C., and FmocCl (905 mg, 3.5 mmol) in CH$_2$Cl$_2$ (6.6 ml) was added dropwise. The mixture was allowed to come to ambient temperature overnight. The solvent was evaporated and the residue was dissolved in THF (7.5 ml) and 1M HCl was added (7.5 ml). This mixture was stirred for 4 hours at ambient temperature. Then chloroform (50 ml) and brine (40 ml) were added and the phases were separated. The aqueous layer was extracted 2 x with CHCl$_3$ (50 ml). The combined organic layer was dried (MgSO$_4$), concentrated and purified by flash chromatography (silica gel, hexane: ethyl acetate: acetic acid=50:50:5). The product containing-fractions were concentrated and lyophilyzed to yield 615 mg (0.928 mmol, 92.8%).

$^1$H NMR (300 MHz, d$_6$-DMSO): δ7.86 (d, 4H, J 7.2 Hz), 7.70 (d, 4H, J 7.5 Hz), 7.41–7.27 (m, 8H), 4.24 (m, 6H), 3.86 (q, 2H, J 4.5 Hz), 1.62 (m, 4H), 1.24 (m, 6H). $^{13}$C NMR (75 MHz, CDCl$_3$): δ174.40, 172.39, 156.30, 144.31, 144.22, 141.10, 129.31, 127.99, 127.68, 127.44, 125.67, 121.77, 120.46, 65.91, 54.66, 47.12, 31.40, 28.68, 25.57, 21.53.

FAB-MS m/z 663 (M$^+$+1);

C$_{39}$H$_{38}$N$_2$O$_8$ (662.73). Calc: C, 70.68; H, 5.78; N, 4.23. Found: C, 71.2; H, 5.62; N, 4.07.

EXAMPLE 7

2,3-Diaminosuccinic acid a) 2,3-Bis(benzylamino)succinic acid

To a mechanically stirred solution of meso-2,3-dibromosuccinic acid (27.6 g, 0.100 mol) in alcohol (200 ml) was slowly added benzylamine (85 g, 0.80 mol) at ambient temperature. After complete addition the mixture was refluxed overnight. A heavy precipitate of salts appeared. The mixture was cooled to 50° C. and concentrated hydrochloric acid was added until pH was 4–5. The precipitate was filtered off, washed several times with water and alcohol and dried.

Yield 24.5 g (75 %).

$^1$H NMR (300 MHz, D$_2$O/NaOD): δ3.08 (2H, s), 3.30 (2H, d, J 13 Hz), 3.55 (2H, d, J 13 Hz), 7.2 (10H, m). $^{13}$C NMR (75 MHz, D$_2$O/NaOD): δ50.9, 64.7, 127.1, 128.5 (br), 139.2, 179.0.

b) meso-2,3-Diaminosuccinic acid

Meso-2,3-bis(benzylamino)succinic acid (9.5 g, 0.029 mol) was dissolved in a mixture of glacial acetic acid (50 ml) and concentrated hydrochloric acid (50 ml). Hydrogenolysis was effected at ambient temperature with 10% palladium on charcoal (1.0 g) as catalyst. The reaction was run until NMR showed that unreacted starting material was no longer present. Water (100 ml) was added and the catalyst was removed by filtration. The filtrate was concentrated (rotavapor) and the residue was dissolved in dilute aqueous sodium hydroxide. pH was adjusted to approximately 5 upon addition of glacial acetic acid. Crystals were filtered off and washed.

Yield 3.8 g (88 %), white solid.

¹H NMR (300 MHz, D₂O/NaOD): δ3.21(s). ¹³C NMR (75 MHz, D₂O/NaOD): δ: 60.3, 180.0.

C₄H₈N₂O₄ Calc.: C 32.44; H 5.44; N 18.91. Found: C 31.51; H 5.41; N 18.32.

c) meso-2,3-Bis(trimethylsilylamino)succinic acid di(trimethylsilyl) ester

The reaction was run under nitrogen. A suspension of meso-2,3-diaminosuccinic acid (296 mg, 2.00 mmol) in hexamethyldisilazane (10 ml) and trimethylchlorosilane (1 ml) was stirred at 100° C. overnight to give a clear solution. Excess silylating reagents were distilled off at reduced pressure. The solid white residue was used directly in acylation reactions.

¹H NMR (300 MHz, CDCl₃): δ0.03 (18H, s), 0.28 (18H, s), 3.5 (2H, m). ¹³C NMR (75 MHz, CDCl₃): δ–0.3, 0.03, 60.9, 174.1.

d) meso-2,3-Bis[(9-fluorenylmethoxycarbonyl)amino]succinic acid

The reaction was run under nitrogen. The silylated diaminosuccinic acid prepared in step (c) was dissolved in dry dichloromethane (10 ml) and cooled to 0° C. A solution of 9-fluorenylmethyl chloroformate (1.14 g, 4.4 mmol) in dry dichloromethane (4 ml) was added. The reaction mixture was stirred overnight and then concentrated. The residue was dissolved in THF (10 ml) and water (approximately 1 ml) was added. The mixture was stirred for 10 minutes and then concentrated. The product was extracted into ethyl acetate, the solution was washed with water, dried (MgSO₄) and filtered. Hexane was added, and the precipitate was filtered off and washed with hexane. Finally the product was purified by column chromatography (silica, hexane/ethyl acetate/acetic acid 1:3:1).

Yield 0.85 g (72 %), white crystals.

¹N NMR (300 MHz, DMSO-d₆): δ=4.1–4.3 (6H, m), 4.5 (2H, d), 7.2–7.4 (12H, m), 7.6–7.7 (4H, m), 7.8–7.9 (4H, m). ¹³C NMR (75 MHz, DMSO-d₆): δ=47.0, 56.1, 66.5, 120.5, 125.9, 127.5, 128.0, 141.0, 144.1, 156.4, 171.1.

FAB-MS Signal at m/z 637.2(3), 631.1(5), 615.2(21), 593.2(2), 435.1(9), 326.3(15), 179.1(100).

e) Racemic-2,3-Bis[(9-fluorenylmethoxycarbonyl)amino]succinic anhydride

A suspension of meso-2,3-bis[(9-fluorenylmethoxycarbonyl)-amino]succinic acid (150 mg, 0.25 mmol) in acetic anhydride was stirred at 120° C. until all material was dissolved (1–2 minutes). Excess anhydride was removed in vacuo. The crude product was used in peptide synthesis without further purification.

¹H NMR (300 MHz, DMSO-d₆): δ4.25 (2H, t), 4.39 (4H, d), 4.80 (2H, d), 7.2–7.4 (8H, m), 7.66 (4H, d), 7.88 (4H, d), 8.30 (2H, d). ¹³C NMR (75 MHz, DMSO-d₆): δ46.8, 55.6, 66.9, 120.6, 125.5, 127.5, 128.1, 141.1, 143.9, 156.4, 168.2.

EXAMPLE 8

(S,S)-2,7-Diamino-E-oct-4-enedioic acid a) 1,4-Bis[(2R,5S)-3,6-dimethoxy-2-isopropyl-2,5-dihydro-5-pyrazinyl]-E-but-2-ene (2R)-2,5-Dihydro-3,6-dimethoxy-2-isopropylpyrazine (5.53g, 30 mmol) was dissolved in anhydrous THF and the solution was cooled to –78° C. A solution of BuLi in hexane (19.62 ml, 31.0 mmol) was added. After 60 minutes at –78° C. a solution of E-1,4-dibromobut-2-ene (3.21g, 15 mmol) in 30 ml THF was added dropwise, and the solution came to ambient temperature overnight. After hydrolysis with phosphate buffer (pH 7) the mixture was extracted with diethyl ether, and the organic layer was washed with water and brine. After drying (MgSO₄) the solvent was evaporated and the residue was purified by flash chromatography (hexane/ethyl acetate 4/1).

Yield: 4.73 g (75%).

¹H NMR (CDCl₃) δ: 0.67(d,6H), 1.04(d,6H), 2.1–2.4(m, 2H), 2.48(dd,4H), 3 67(s,6H), 3.68(s,6H), 3.93(dd,2H), 4.03(dd,2H), 5.35(dd,2H) ¹³C-(CDCl₃) δ: 16.52, 19.07, 31.61, 37.09, 52.16, 52.23, 55.62, 60.60, 128.50.

C₂₂H₃₆N₄O₄ (420) Calc: C, 62.86; H, 8.57. Found: C, 62.65; H, 8.62.

b) Dimethyl (S,S)-2,7-diamino-E-oct-4-enedioate

A solution of 1,4-bis[(2R,5S)-3,6-dimethoxy-2-isopropyl-2,5-dihydro-5-pyrazinyl]-E-but-2-ene (4.02g, 9.9 mmol) in 40 ml dioxane and 20.0 mmol HCl (1.67 ml) in 38 ml water was stirred at ambient temperature for 4 hours, and the solution was extracted with diethyl ether. Aqueous ammonia solution was added until a pH of 9 was reached, and the solution was extracted with chloroform. The organic layer was dried (MgSO₄). The valine methyl ester was distilled under vacuum (0.04 torr, ambient temperature).

Yield: 1.92 g (84.3%).

¹H NMR (CDCl₃) δ: 1–70(s,4H), 2.20–2.60(m,4H), 3.51 (dd,2H), 3.69(s,6H), 5.46(dd,2H) ¹³C-(CDCl₃) δ: 37.99, 52.00, 54.11, 128.84, 175.32.

c) (S,S)-2,7-Diamino-E-oct-4-enedioic acid.2 HCl

Dimethyl (S,S)-2,7-diamino-E-oct-4-enedioate (1.65g, 7.17 mmol) was dissolved in 6N HCl (10 ml, 60 mmol), and refluxed under N₂ for 2 hours. The solvent was evaporated, the residue dissolved in 10 ml water and crystallized by the addition of EtOH (100 ml). The crystals were filtered off.

Yield: 1.32 g=67%.

¹H NMR(D₂O) δ: 2.53(dd,4H), 3.97(dd,2H), 5.52(dd,2H) ¹³C-(D₂O) δ: 33.57, 53.07, 128.85, 171.49.

FAB-MS signal at m/z 405.3(11), 203.2(100), 157.1(19), 130.1(7), 93.0(18), 73.9(13).

C₈H₁₆N₂O₄Cl₂ (275), Calc: C, 34.91; H, 5.81; N, 10.18; Cl, 25.78. Found: C, 36.58; H, 5.80; N, 9.70; Cl, 26.01.

d) (S,S)-2,7-Bis(9-fluorenylmethyloxycarbonylamino)-E-oct-4-enedioic acid (S,S)-2,7-Diamino-E-oct-4-enedioic acid dihydrochloride (1.59 g, 5.8 mmol) was suspended in HMDS (20 ml) and TMSCl and refluxed overnight. The solvents were removed, and the residue was dissolved in anhydrous dichloromethane. This solution was cooled to 0° C. and a solution of FmocCl (3.10 g, 12 mmol) in dichloromethane was added. The solution was stirred for 1 hour at this temperature and overnight at ambient temperature. The solvent was evaporated and the residue dissolved in THF. After addition of 1N aqueous HCl the solution was stirred for two hours, extracted with chloroform and dried (MgSO₄). The residue was dissolved in dichloromethane and crystallized by the addition of diethylether.

Yield: 2.50 g (66.8%).

¹H-(DMSO) δ: 2.2–2.4(s,4H), 3.6(s,2H), 3.9–4.5(m,8H), 5.55(s,2H), 7.2–8.1(m,16H) ¹³C-(DMSO) δ: 33.98, 46.56, 53.93, 65.49, 119.66, 124.81, 126.61, 127.17, 127.98, 140.19, 143.28, 155.43, 172.59.

$C_{38}N_{34}N_2O_8$ (646) Calc.: C, 70.59; N, 5.26; N, 4.33. Found: C, 70.17; N, 5.58; N, 4.08.

FAB-MS signal at m/z 661.3 (3), 647.4 (3), 191.2(17), 179.2(100), 165.1(18), 78.9(31).

EXAMPLE 9

[S,S)-2,7-Diamino-Z-oct-4-enedioic acid a) 1,4-Bis[(2R,5S)-3,6-dimethoxy-2-isopropyl-2,5-dihydro-5-pyrazinyl]-Z-but-2-ene (2R)-2,5-Dihydro-3,6-dimethoxy-2-isopropylpyrazine (7.3g, 39.2 mmol) was dissolved in anhydrous THF and the solution was cooled to –78° C. A solution of BuLi in hexane (24.50 ml, 39.2 mmol) was added. After 15 minutes at –78° C., 16.9 ml 1,3-dimethyl-2-imidazolinedione (156 mmol) were added, and after 5 minutes a solution of Z-1,4-dichlorobut-2-ene (2.45 g, 19.6 mmol) in 10 ml THF was added dropwise, and the solution was stirred for 6 hours and kept at –20° C. overnight. After hydrolysis with phosphate buffer (pH=7) the mixture was extracted with diethyl ether, and the organic layer was washed with water and brine. After drying ($MgSO_4$) the solvent was evaporated and the residue was purified by flash chromatography (hexane/ethyl acetate 9/1).

Yield: 710 mg (10.2%).

¹H NMR ($CDCl_3$) δ: 0.67 (d,6H), 1.03 (d,6H), 2.25 (m,2H), 2.55 (m,4H), 3.66 (s,6H), 3.68 (s,6H), 3.91 (dd,2H), 4.07 (m,2H), 5.38 (dd,2H) ¹³C NMR ($CDCl_3$) δ: 16.50, 19.01, 31.57, 32.01, 52.22, 52.31, 55.46, 60.67, 127.30, 163.19, 163.66.

b) Dimethyl (S,S)-2,7-diamino-Z-oct-4-enedioate

A solution of 1,4-bis[(1S,4R)-3,6-dimethoxy-4-isopropyl-2,5-dihydropyrazinyl]-Z-but-2-ene (0.23g, 0.55 mmol) in 30 ml dioxane and 2.2 mmol HCl (0.183 ml) in 10 ml water was stirred at ambient temperature for 12 hours, and the solution was extracted with diethylether. Aqueous ammonia solution was added until pH 9 was reached, and the solution was extracted with chloroform. The organic layer was dried ($MgSO_4$). The valine methyl ester was distilled off (0.02 torr, ambient temperature).

Yield: 0.127g (85 %).

¹H NMR ($CDCl_3$) δ: 1.54 (s,4H), 2.3–2.6 (m,4H), 3.52 (dd,2H), 3.71 (s,6H), 5.54 (m,2H) ¹³C NMR ($CDCl_3$) δ: 32.55, 52.02, 54.17, 127.94, 175.67.

c) (S,S)-2,7-Diamino-Z-oct-4-enedioate acid.2 HCl

To a solution of dimethyl (S,S)-2,7-diamino-Z-oct-4-enedioate (0.108 g, 0.47 mmol) in 0.7 ml methanol a 2N solution of LiOH in water (1.41 mmol., 0.71 ml) was added. The solution was stirred at ambient temperature overnight and then acidified by dropwise addition of 1N HCl. The crystals were filtered off.

Yield: 50 mg (38.7%).

¹H NMR($D_2O$) δ: 2.58(m,4H), 3.99(m,2H), 5.51(m,2H) ¹³C NMR($D_2O$) δ: 27.59, 52.20, 126.84, 171.10.

d) (S,S)2,7-Bis(9-fluorenylmethyloxycarbonylamino)-Z-oct-4-enedioic acid (S,S)-2,7-Diamino-Z-oct-4-enedioic acid (0.050 g, 0.25 mmol) and $Na_2CO_3$ (0.21 g, 20.0 mmol) were dissolved in 3 ml water and 2 ml dioxane. The solution was cooled to 0° C. and a solution of FmocCl (0.26 g, 1.0 mmol) in 1 ml dioxane was added. This mixture was stirred at 0° C. for 3 hours and came to ambient temperature overnight. After extraction with diethyl ether it was acidified by addition of hydrochloric acid. The solution was extracted with chloroform and the amino acid was crystallized from chloroform/hexane. The compound was further purified by flash chromatography (chloroform/acetic acid 9/1).

Yield: 90.0 mg (55.9%).

¹H NMR (DMSO) δ: 2.12–2.64 (m, 4H), 3.88 (s, 2H), 4.04–4.37 (m, 6H), 5.42 (s, 2H), 7.02 (s, 2H), 7.20–8.00 (m, 16H). ¹³C NMR(DMSO) δ: 29.77, 46.88, 55.53, 65.66, 120.23, 125.43, 127.23, 127.74, 129.08, 140.84, 144.11, 155.59, 174.10.

FAB-MS signal at m/z 676.2(2), 587.5(5), 447.4(10), 419.3(45), 391.3(100), 363.3(38), 261.2(45), 233.2(29).

EXAMPLE 10

(S,S)-2,7-Diamino-oct-4-ynedioic acid a) 1,4-Bis((2R,5S)-3,6-dimethoxy-2-isopropyl-2,5-dihydro-5-pyrazinyl]but-2-yne To a solution of (2R)-2,5-dihydro-3,6-dimethoxy-2-isopropylpyrazine (4.605 g, 25 mmol) and 1,3-dimethyl-2-imidazolidinone (11.4 g, 102 mmol) in THF (48 ml) 1.6M n-BuLi (16 ml, 25.5 mmol) was added dropwise. After 1 hour a solution of 1,4-dichloro-2-butyne (1.54 g, 12.5 mmol) in THF (8 ml) was added dropwise. The mixture was allowed to come to ambient temperature overnight and quenched with 1M phosphate buffer (pH 7). The mixture was diluted with diethyl ether (150 ml) and water (40 ml) and the layers separated. The aqueous layer was extracted twice with ether (2×150 ml) and the combined organic layers dried ($MgSO_4$), filtered, concentrated and purified by flash chromatography (silica gel, hexanes: ether=7:1).

Yield 3.325 g (7.94 mmol, 63.6%).

¹H-NMR (300 MHz, $CDCl_3$): δ4.05–3.99 (m, 4H), 3.68 (s, 6H, 3.67 (s, 6H), 2.70 (dd, 2H, J -14.1,3.0 Hz), 2.57 (dd, 2H, J -14.1,3.0 Hz), 2.26 (dsept, 2H, J 6.9,3.0 Hz), 1.05 (d, 6H, J 6.9 Hz), 0.64 (d, 6H, J 6.9 Hz); ¹³C NMR (75 MHz, $CDCl_3$): δ164.56, 161.53, 77.52, 60.51, 54.46, 52.34, 52.22, 31.43, 25.26, 19.07, 16.40.

FAB-MS m/z 419 ($M^+$+1).

$C_{22}H_{34}N_4O_4$ (418.53). Calc: C, 63.14; H, 8.19; N, 13.39. Found: C, 63.27; H, 8.12, N, 13.54.

b) Dimethyl (S,S)-2,7-diamino-oct-4-ynedioate 1,4-Bis((2R,5S)-3,6-dimethoxy-2-isopropyl-2,5-dihydro-5-pyrazinyl)-but-2-yne (920 mg, 2.2 mmol) was dissolved in dioxane (18 ml) and 0.5M HCl (18 ml) and stirred at ambient temperature for 12 hours. This mixture was washed with diethyl ether (30 ml ), the aqueous layer was brought to pH 9 by addition of 25% ammonia in water, and quickly extracted with $CHCl_3$ (3×75 ml). The organic layer was dried with $MgSO_4$, filtered, and concentrated. The methyl valinate was removed by kugelrohr distillation (25°–50° C., 0.01 torr).

Yield 486 mg (2.13 mmol, 96.8%) of a yellow oil.

$^1$H-NMR (300 MHz, CDCl$_3$): δ3.74 (s, 6H), 3.59 (t, 2H, J 5.4 Hz), 2.60 (d, 4H, J 5.4 Hz); $^{13}$C NMR (75 MHz, CDCl$_3$): δ174.46, 78.31, 53.31, 52.22, 25.15.

c) (S,S)-2,7-Diamino-Z-oct-4-ynedioic acid.2 HCl

A solution of dimethyl (S,S)-2,7-diamino-oct-4-ynedioate (450 mg, 1.97 mmol) was heated in 6M HCl (7.2 ml) to 50 to 60° C. for 12 hours under N$_2$. The volatile compounds were evaporated (rotavap, water bath 40° C.). The residue was dissolved in water (1 ml, turbid), ethanol was added (20 ml) and slow addition of ether led to a white, crystalline precipitate. This mixture was kept for 12 hours in the refrigerator, filtered, washed with ether and dried under vacuum.

Yield 399 mg (1.46 mmol, 74.2%).

$^1$H NMR (300 MHz, D$_2$O/DCl): δ4.18 (t, 2H, J 4.8 Hz), 2.85 (m,AA'X, 4H); $^{13}$C NMR (75 MHz, D$_2$O/DCl)): δ172.62, 79.88, 53.75, 22.60.

FAB-MS m/z 201 (M$^+$–72).

d) (S,S) -2,7-Bis(9-fluorenylmethyloxycarbonylamino)-oct-4-ynedioic acid

A solution of (S,S)-2,7-diamino-Z-oct-4-ynedioic acid-2 HCl (400 mg, 1.46 mmol) in dioxane and 1M Na$_2$CO$_3$-solution (10.22 ml, 10.22 mmol) was cooled to 0° C. and a solution of FmocCl (1.14 g, 4.39 mmol) in 4 ml dioxane was added. This mixture was stirred at 0° C. for 1 hour and allowed to come to ambient temperature overnight. After extraction with diethyl ether (2×50 ml) the aqueous layer was acidified by addition of diluted HCl. The solution was extracted with chloroform (3×50 ml), dried (MgSO$_4$) and concentrated. The residue was purified by flash chromatography (silica gel, hexane:ethyl acetate:acetic acid=10:10:1).

Yield 376 mg (0.58 mmol, 39%).

$^1$H NMR (300 MHz, DMSO): δ7.87 (d, 4H, J 7.5 Hz), 7.73 (d, 4H, J 7.5 Hz), 7.41 (t, 4H, J 7.5 Hz), 7.33 (t, 4H, J 7.5 Hz), 4.26 (m, 8H), 2.52 (m, 4H); $^{13}$C(DMSO) δ170.43, 154.62, 152.58, 142.32, 139.47, 126.22, 125.94, 124.35, 119.12, 77.68, 65.45, 53.08, 46.57, 21.77.

FAB-MS m/z 645 (M$^+$+1).

C$_{38}$H$_{32}$N$_2$O$_8$ (644.67). Calc: C, 70.80; H, 5.00; N, 4.35. Found: C, 69.20; H, 5.34; N, 4.13.

EXAMPLE 11

(2S,4R,5R,7S)-2,7-Diamino-4,5-dihydroxy-4,5-O,O-isopropylideneoctanedioic acid a) (2R,3R)-1,4-Bis(2R,5S)-3,6,dimethoxy-2-isopropyl-2,5-dihydro-5-pyrazinyl)-2,3-dihydroxy-2,3-O,O-isopropylidene-butane (2R)-2,5-dihydro-3,6-dimethoxy-2-isopropylpyrazine (7.36 g, 40 mmol) was dissolved in anhydrous THF and the solution was cooled to −78° C. A solution of BuLi in hexane (40.0 mmol, 25 ml) was added. After 20 minutes at −78° C. a solution of (2R,3R)-1,4-dibromo-2,3-dihydroxy-2,3-O-isopropylidene-butane (3.78 g, 13.1 mmol)in 10 ml THF was added dropwise, and the solution was kept at 4° C. for 36 hours. After hydrolysis with phosphate buffer (pH 7) the mixture was extracted with diethyl ether, and the organic layer was washed with water and brine. After drying (MgSO$_4$) the solvent was evaporated and the residue was purified by repeated crystallization from acetonitrile.

Yield: 3.70 g (57%).

$^1$H NMR (CDCl$_3$) δ: 0.68(d,6H), 1.03(d,6H), 1.34(s,6H), 1.95–2.15(m,4H), 2.24(m,2H), 3.65(s,6H), 3–67(s,6H), 3.94(m,2H), 4.04(m,2H), 4.11(m,2H). $^{13}$C NMR (CDCl$_3$) δ: 16.91, 19.05, 27.39, 31.73, 38.32, 52.27, 52.36, 52.70, 60.60, 77.89, 108.19, 163.66, 163.70.

FAB-MS signal at m/z 495.4(100).

C$_{25}$H$_{42}$N$_4$O (494): Calc: C, 60.71; H, 8.56; N, 11.33. Found: C, 60.76; H, 8.32; N, 11.36.

b) Dimethyl (2S,4R,5R,7S)-2,7-diamino-4,5-dihydroxy-4,5-O,O-isopropylideneoctanedioate (2R,3R)-1,4-Bis((2R,5S)-3,6-dimethoxy-2-isopropyl-2,5-dihydro-5-pyrazinyl)-2,3-dihydroxy-2,3-O,O-isopropylidenebutane (1.22 g, 2.47 mmol) was dissolved in 10 ml dioxane and 20 ml MeOH. A solution of 9.88 mmol HCl in 10 ml water was added and the solution was stirred at ambient temperature overnight. The solvents were removed, the residue dissolved in water and extracted with diethyl ether. To the aqueous layer ammonia was added until pH 9 was reached, and it was extracted with chloroform. After drying (MgSO$_4$) the solvent was removed and the valine methyl ester was distilled off (30°–40° C., 0.04 Torr).

Yield: 0.67 g (89.3%).

$^1$H NMR (CDCl$_3$) δ: 1.34(s,6H), 1.64(br s, 4H), 1.72–1.84(m,2H), 1.99–2.08(m,2H), 3.65(m,2H), 3.71 (s,6H), 3.80 (m, 2H). $^{13}$C NMR (CDCl$_3$) δ: 27.17, 37.54, 52.04, 52.74, 78.78, 108.99, 175.51.

c) (2S,4R,5R,7S)-2,7-Diamino-4,5-dihydroxy-4,5-O,O-isopropylideneoctanedioic acid Dimethyl (2S,4R,5R,7S)-2,7-diamino-4,5-dihydroxy-4,5-O,O-isopropylideneoctanedioate (0.62 g, 2.04 mmol) was dissolved in 2.5 ml dioxane and 2.1 ml 2N LiOH solution in water (4.1 mmol) were added and the solution was stirred under argon overnight. TLC indicated quantitative formation of the title compound. The crude reaction solution was used in the next step.

d) (2S,4R.5R,7S)-2.7-Bis(9-fluorenylmethyloxycarbonylamino)4,5-dihydroxy-4,5-O,O-isopropylideneoctanedioic acid The crude solution of (2S,4R,5R,7S)-2,7-diamino-4,5-dihydroxy-4,5-O,O-isopropylideneoctanedioic acid (2.04 mmol) was cooled to 0° C. and 10 ml dioxane and 10 ml 1N NaOH solution (10 mmol) were added. Then 2.07 g FmocCl (8.0 mmol) were added in small portions and the mixture was stirred at 0° C. for 5 hours and at ambient temperature overnight. The mixture was extracted with diethyl ether and acidified by the addition of KHSO$_4$. After extraction with CHCl$_3$ the organic layer-was dried (MgSO$_4$) and the solvent was removed. Excess unreacted FmocCl was removed by silica gel filtration in acetone/MeOH and the residue was purified by precipitation from CHCl$_3$/EtOEt.

Yield: 0.49 g (33.6%).

$^1$H NMR (DMSO/D$_2$O) δ: 1.20(s,6H), 1.73(m,2H), 1.99(m,2H), 3.87(m,2H), 4.14–4.24(m,6H), 7.23–7.82(m, 16H). $^{13}$C NMR (DMSO) δ: 27.78, 36.21, 47.27, 53.75, 66.19, 78.82, 107.89, 120.67, 125.81, 127.76, 128.32, 141.24, 144.39, 156.12, 175.96.

FAB-MS signal at m/z 563.2(2), 179.1(100) C$_{41}$H$_{40}$N$_2$O$_{10}$ (720): Calc: N, 3.89, Found: N, 3.81.

EXAMPLE 12

(2S,4S,5S,7S)-2,7-Diamino-4,5-dihydroxy-4,5-O,O-isopropylideneoctanedioic acid a) (2S,3S)-1,4-Bis((2R,5S)-3,6-dimethoxy-2-isopropyl-2,5-dihydro-5-pyrazinyl)-2,3-dihydroxy-2,3-O,O-isopropylidene-butane (2R)-2,5-dihydro-3,6-dimethoxy-2-isopropylpyrazine (9.59 g, 52.1 mmol) was dissolved in anhydrous THF and the solution was cooled to −78° C. A solution of BuLi in hexane (52 mmol, 32.5 ml) was added. After 60 minutes at −78° C. a solution of (2S,3S)-1,4-dibromo-2,3-dihydroxy-2,3-O,O-isopropylidene-butane (6.0 g, 20.83 mmol) in 10 ml THF was added dropwise, and the solution came to ambient temperature overnight and was stirred for an additional 24 hours. After hydrolysis with phosphate buffer (pH 7) the mixture was extracted with diethyl ether, and the organic layer was washed with water and brine. After drying (MgSO$_4$) the solvent was evaporated and the residue was purified by repeated crystallization from MeCN.

Yield: 3.43 g (33.3%).

$^1$H NMR (CDCl$_3$) δ: 0.70(d,6H), .1.03(d,6H), 1.44(s,6H), 2.15–2.30(m,4H), 3.66(s,6H), 3.69(s,6H), 3.92(m,2H), 4.04 (m,2H), 4.09–4.20(m,4H). $^{13}$C NMR (CDCl$_3$) δ: 16.78, 19.11, 27.67, 31.88, 38.38, 52.37, 52.44, 52.83, 60.84, 77.65, 108.57, 163.15, 163.88.

FAB-MS signal at m/z 495.4(53), 253.2(40), 197.2(58), 141.1(100).

C$_{25}$H$_{42}$N$_4$O (494) Calc: C, 60.71; H, 8.56; N, 11.33; Found: C, 60.89; H, 8.42; N, 11.45.

b) Dimethyl (2S,4S,5S,7S)-2,7-diamino-4,5-dihydroxy-4,5-O,O-isopropylideneoctanedioate (2S,3S)-1,4-Bis((2R,5S)-3,6-dimethoxy-2-isopropyl-2,5-dihydro-5-pyrazinyl)-2,3-dihydroxy-2,3-O,O-isopropylidenebutane (2.5 g, 5.06 mmol) was dissolved in 40 ml dioxane. A solution of 20.0 mmol HCl in 40 ml water was added and the solution was stirred at ambient temperature overnight. The solvents were removed, the residue dissolved in water and extracted with diethyl ether. To the aqueous layer ammonia was added until pH 9 was reached, and it was extracted with chloroform. After drying (MgSO$_4$) the solvent was removed and the valine methyl ester was distilled off (30°–40° C., 0.04 Torr).

Yield: 1.507 g (98.0%).

$^1$H NMR (CDCl$_3$) δ: 1.32(s,6H), 1.53(br s, 4H), 1.60–1.68(m,2H), 1.85–1.94(m,2H), 3.63(m,2H), 3.67 (s,6H), 3.80(m,2H). $^{13}$C NMR (CDCl$_3$) δ: 27.25, 37.20, 51.96, 52.74, 77.58, 108.80, 176.10.

c) (2S,4S,5S,7S)-2,7-Diamino-4,5-dihydroxy-4,5-O,O-isopropylidene-octanedioic acid Dimethyl (2S,4S,5S,7S)-2,7-diamino-4,5-dihydroxy-4,5-isopropylideneoctanedioate (1.51 g, 4.96 mmol) was dissolved in 5 ml dioxane and 4.95 ml 2N LiOH solution in water (9.91 mmol) were added and the solution was stirred under argon overnight. TLC indicated quantitative formation of (2S,4S,5S,7S)-2,7-diamino-4,5-dihydroxy-4,5-O,O-isopropylideneoctanedioic acid. The crude reaction solution was used in the next step.

d) (2S,4S,5S,7S )-2,7-Bis(9-fluorenylmethyloxycarbonylamino)-4,5-dihydroxy-4,5-O,O-isopropylideneoctanedioic acid The crude solution of (2S,4S,5S,7S)-2,7-diamino-4,5-dihydroxy-4,5-O,O-isopropylideneoctanedioic acid (4.96 mmol) was cooled to 0° C., and 16 ml 1N NaOH solution (16 mmol) were added. Then a solution of 3.89 g FmocCl (15.0 mmol) in 16 ml dioxane was added in small portions and the mixture was stirred at ambient temperature for 90 minutes. The solution was acidified by the addition of KHSO$_4$. After extraction with CHCl$_3$ the organic layer was dried (MgSO$_4$) and the solvent was removed. An aliquot of the residue was purified by flash chromatography (hexane/ethyl acatate/acetic acid 5/5/1).

Yield: 1.69(46%).

$^1$H NMR (DMSO/D$_2$O) δ: 1.23(s,6H), 1.7–2.0(m,4H), 3.62 (m, 2H), 4.02 (m, 2H), 4.1–4.35 (m, 6H), 7.2–7.9 (m, 16H). $^{13}$C NMR (DMSO) δ: 27.94, 34.59, 47.39, 52.29, 66.45, 77.49, 109.13, 120.90, 125.91, 127.97, 128.59, 141.44, 144.44, 157.02, 174.75.

FAB-MS signal at m/z 743.3(28), 563.2(58), 505.2(72).

C$_{41}$H$_{40}$N$_2$O$_{10}$ (720) Calc: N, 3.89; Found: N, 4.09.

EXAMPLE 13

(2S,4R,5S,7S)-2,7-Diamino-4,5-dihydroxy-4,5-isopropylideneoctanedioic acid a) (2R,3S)-1,4-Bis[(2R,5S)-3,6-dimethoxy-2.-isopropyl-2,5-dihydro-5-pyrazinyl]-2,3-dihydroxy-2,3-O,O-isopropylidene-butane (2R)-2,5-dihydro-3,6-dimethoxy-2-isopropylpyrazine (6.08 g, 33.0 mmol) was dissolved in anhydrous THF and the solution was cooled to −78° C. A solution of BuLi in hexane (33.0 mmol, 20.6 ml) was added. After 45 minutes at −78° C. a solution of (2R,3S)-1,4-dibromo-2,3-dihydroxy-2,3-O-isopropylidene-butane (4.52 g, 15.70 mmol) in 10 ml THF was added dropwise, and the solution came to ambient temperature overnight and was stirred for an additional 24 hours. After hydrolysis with phosphate buffer (pH 7) the mixture was extracted with diethyl ether, and the organic layer was washed with water and brine. After drying (MgSO$_4$) the solvent was evaporated and the residue was purified by flash chromatography (hexane/ethyl acetate 9/I).

Yield: 0.77 g (10.0%).

$^1$H NMR (CDCl$_3$) δ: 0.68(m,6H), 1.03(m,6H), 1.32(s, 3H), 1.45(s, 3H), 1.30–1.55 (m, 1H), 1.85–2.30 (m, 5H), 3.62(s, 3H), 3.66(s,3H), 3.68(s,6H), 3.92(m,2H), 4.06–4.26(m,3H), 4.45(m,1H). $^{13}$C NMR (CDCl$_3$) δ: 16.62, 16.77, 19.04, 19.08, 26.20, 28.49, 31.71, 31.91, 33.69, 35.07, 52.21, 52.27, 52.32, 52.35, 52.40, 52.98, 60.58, 60.80, 74.31, 74.66, 107.16, 163.03, 163.40, 163.91, 164.30.

b) Dimethyl (2S,4R,5S,7S)-2,7-diamino-4,5-dihydroxy-4,5-O,O-isopropylideneoctanedioate (2R,3S)-1,4-Bis((2R,5S)-3,6-dimethoxy-2-isopropyl-2,5-dihydro-5-pyrazinyl)-2,3-dihydroxy-2,3-O,O-isopropylidenebutane (0.77 g, 1.55 mmol) was dissolved in 2 ml dioxane. A solution of 6.0 mmol HCl in 12 ml water was added and the solution was stirred at ambient temperature for 5 hours. Ammonia was added until pH9 was reached, and the solution was extracted with chloroform. After drying (MgSO$_4$) the solvent was removed and the valine methyl ester was distilled off (30°–40° C., 0.05 Torr).

Yield: 0.36 g (77%).

$^1$H NMR (CDCl$_3$) δ: 1.30(s,3H), 1.41(s,3H), 1.40–1.48 (m, 1H), 1.72 (s, 4H), 1.75–2.00 (m, 3H), 3.60–3.67(m,2H), 3.70(s,6H), 4.20–4.40(m,2H). $^{13}$C NMR (CDCl$_3$) δ: 25.81, 28.26, 34.69, 34.89, 51.55, 52.00, 52.02, 52.66, 74.26, 75.20, 108.23, 175.43, 176.51.

c) (2S,4R,5S,7S)-2,7-Diamino-4,5-dihydroxy-4,5-O,O-isopropylideneoctanedioic acid Dimethyl (2S,4R,5S,7S)-2,7-diamino-4,5-dihydroxy-4,5-isopropylideneoctanedioate (0.36 g, 1.19 mmol) was dissolved in 5 ml dioxane and 1.19 ml 2N LiOH solution in water (2.38 mmol) were added and the solution was stirred under argon overnight. TLC control indicated quantitative formation of (2S,4R,5S,7S)-2,7-diamino-4,5-dihydroxy-4,5-O,O-isopropylideneoctanedioic acid. The crude reaction solution was used in the next step.

d) (2S,4R,5S,7S)-2,7-Bis(9-fluorenylmethyloxycarbonylamino)-4,5-dihydroxy-4,5-O,O-isopropylideneoctanedioic acid The crude solution of (2S,4R,5S,7S)-2,7-diamino-4,5-dihydroxy-4,5-O,O-isopropylideneoctanedioic acid (1.19 mmol) was cooled to 0° C., and 4.0 ml 1N NaHCO$_3$ solution (4.0 mmol) were added. Then a solution of 1.03 g FmocCl (4.0 mmol) in 4 ml dioxane was added in small portions and the mixture was stirred at ambient temperature for 60 minutes. The solution was acidified by the addition of KHSO$_4$. After extraction with CHCl$_3$ the organic layer was dried (MgSO$_4$) and the solvent was removed. The residue was purified by flash chromatography (hexane/ethyl acetate/acetic acid 5/5/1).

Yield: 0.566 g (66%).

$^1$H NMR (DMSO, D$_2$O) δ: 1.16(s,3H), 1.30(s,3H), 1.50–2.05(m,4H), 3.80–4.40(m,8H), 7.15–8.0(m,16H). $^{13}$C NMR (DMSO, D$_2$O) δ: 26.63, 29.05, 31.50, 31.94, 47.43, 51.52, 52.19, 66.50, 74.10, 75.10, 108.36, 120.88, 125.93, 127.98, 128.60, 141.48, 144.39, 144.76, 156.82, 157.12, 174.11, 175.11.

EXAMPLE 14

(S,S)2,6-Diamino-4-oxaheptanedioic acid a) Bis[(2R,5S)-2,5-dihydro-3,6-dimethoxy-2-isopropyl-5-pyrazinyl]methyl ether Butyl lithium in hexane (1.6M, 6.25 ml, 10.0 mmol) was added to a solution of (2R)-2,5-dihydro-3,6-dimethoxy-2-isopropylpyrazine (1.84 g, 10.0 mmol) in dry THF (8 ml) at −78° C. The mixture was stirred for 15 minutes. A solution of bis(chloromethyl) ether (0.67 g, 5.0 mmol) in dry THF (2 ml) was added. The reaction mixture was allowed to reach ambient temperature overnight. The solvent was evaporated and the residue was taken up in diethyl ether. The ether solution was washed with water, dried (MgSO$_4$) and evaporated. The product was purified by chromatography (silica gel, hexane/ethyl acetate 2:1).

Yield: 0.65 g (32%), yellow oil.

$^1$H NMR (300 MHz, CDCl$_3$): δ0.63 (6H, d), 1.05 (6H, d), 2.25 (2H, m), 3.58 (2H, dd), 3.63 (6H, s), 3.64 (6H, s), 3.76 (2H, dd), 3.83 (2H, t), 3.98 (6H, m). $^{13}$C NMR (75 MHZ, CDCl$_3$): δ16.4, 19.1, 30.1, 52.1, 52.2, 56.9, 60.3, 72.5, 161.0, 165.0.

b) Dimethyl (S,S)-2,6-diamino-4-oxaheptanedioate

Bis[(2R,5S)-2,5-dihydro-3,6-dimethoxy-2-isopropyl-5-pyrazinyl]methyl ether (0.65 g, 1.49 mmol) was dissolved in methanol (5 ml) and 0.25M hydrochloric aid (23.8 ml, 5.96 mmol) was added. The mixture was stirred at ambient temperature overnight. The water/methanol solution was extracted with diethyl ether. pH was then adjusted to 10 by addition of ammonia, and D-valine methyl ester was extracted into ether. Most of the water was evaporated. The residue was used in the next step without further purification.

$^1$H NMR (300 MHz, DMSO-d$_6$): δ3.72 (6H, s), 3.85 (4H, m), 4.23 (2H, t). $^{13}$C NMR (75 MHz, CDCl$_3$): δ52.8, 53.2, 68.9, 168.4.

c) (S,S)-2,6-Diamino-4-oxaheptanedioic acid.2 HCl

The dimethyl ester from above was refluxed in 6M hydrochloric acid (5 ml) for 3 hours. The solution was evaporated and freeze dried.

Yield: 420 mg of white solid.

$^1$H NMR (300 MHz, D$_2$O): δ3.87 (2H, dd, J 10.8 Hz, J 3.2 Hz), 3.95 (2H, dd, J 10.8 Hz J 4.6 Hz), 4.13 (2H, dd, J 3.2 and 4.6 Hz). $^{13}$C NMR (75 MHz, CDCl$_3$): δ53.4, 68.4, 170.3.

d) (S,S)-2,6-Bis[(9-fluorenylmethoxycarbonyl)amino]-4-oxaheptanedioic acid

The reaction was run under nitrogen. A suspension of (S,S)-2,6-diamino-4-oxaheptanedioic acid dihydrochloride (200 mg, 0.75 mmol) in hexamethyldisilazane (10 ml) and chlorotrimethylsilane (1 ml) was heated at 120° C. for 3 hours to give a clear solution. Excess silylating reagents were removed in vacuo and the reside was dissolved in dry dichloromethane (5 ml). The solution was cooled to 0° C. and a solution of 9-fluorenyl chloroformate (425 mg, 1.65 mmol) in dry dichloromethane (2 ml) was added. The mixture was stirred for 2 hours and then evaporated. The residue was taken up in THF (5 ml) and 1 ml 0.1M hydrochloric acid was added. The mixture was stirred for 15 minutes and then evaporated. The residue was taken up in ethyl acetate. The organic phase was washed with water, dried (MgSO$_4$) and evaporated. The product was purified by column chromatograpy (silica, chloroform/methanol/acetic acid 85:10:5).

Yield: 310 mg (65%), white solid.

$^1$H NMR (300 MHz, DMSO-d$_6$): δ3.7 (4H, m), 4.1 (2H, m), 4.25 (6H, m), 7.2–7.4 (10H, m), 7.7 (4H, d), 7.8 (4H, d).

EXAMPLE 15

(S,S)-2,7-Diamino-4-azaoctanedioic acid a) (S,S)-2,7-Bis(tert-butyloxycarbonylamino)-4-azaoctanedioic acid

A solution of (S)-4-amino-2-tert-butyloxycarbonylaminobutyric acid (1.03 g, 4.70 mmol) in acetonitrile (50 ml) was added to a solution of (S)-Boc-serine-β-lactone (0.80 g, 4.27 mmol) in acetonitrile (50 ml) and degassed H$_2$O (50 ml). The pH was maintained at 5.5 by dropwise addition of 1M NaHCO$_3$ with stirring. The mixture was stirred for 5 days at ambient temperature. The pH was controlled by NaHCO$_3$ addition and the reaction monitored by TLC. The solvents were distilled off, the residue triturated with chloroform (5 ml), to which acetic acid was added to give pH 5.

The chloroform solution was evaporated and the product isolated after chromatography on silica gel (CHCl$_3$: MeOH 2:1).

Yield: 0.92 g (53%) of a white solid.

$^1$H NMR (DMSO-d$_6$, 300 MHz): δ7.33 (d, J 6.3 Hz; 1H), 6.27 (d, J 5.7 Hz; 1H), 4.42 (d, J 7.5 Hz; 1H), 4.15 (dd, J$_1$ 10.5 Hz, J$_2$ 3.9 Hz; 1H), 4.01 (d, J 6.3 Hz; 1H), 3.87 (br s; 1H), 2.78 (br s; 1H), 1.78–2.21 (m; 4H), 1.36 and 1.35 (2 s; 18H). $^{13}$C NMR (DMSO-d$_6$, 75.43 MHz): δ174.95, 155.74, 155.25, 79.58, 78.22, 78.04, 62.97, 56.42, 56.00, 51.17, 48.99, 38.14, 28.62, 28.46.

C$_{17}$H$_{31}$N$_3$O$_8$ (405.45).

b) (S,S)-2,7-Bis(tert-butyloxycarbonylamino)-4-(benzyloxycarbonyl)-4-azaoctanedioic acid 1M NaHCO$_3$ (5.9 ml, 5.92 mmol) and benzyloxycarbonyl chloride (0.5 g, 0.42 ml, 2.96 mmol) were added to a solution of (S,S)-2,7-bis (tert-butyloxycarbonylamino)-4-azaoctanedioic acid (0.6 g, 1.48 mmol) in dioxane (40 ml) and H$_2$O (30 ml) at 0° C. The mixture was stirred at 0° C. for 3 hours, at ambient temperature for 6 hours, evaporated, the residue triturated with chloroform (5 ml) and acetic acid to pH 5. The chloroform solution was evaporated and the product isolated after chromatography on silica gel (CHCl$_3$: MeOH 4:1).

Yield: 0.39 g (50%) of a white solid.

$^1$H NMR (DMSO-d$_6$, 300 MHz): δ7.21–7.37 (m, 5H), 7.18 (d, J 7.8 Hz; 1H), 6.23 (d, J 6.3 Hz; 1H), 4.98 (s, 2H), 4.43 (dd, J 10.8 Hz, J 3.3 Hz; 1H), 4.09 (dd, J 10.2 Hz, J 6.3 Hz; 1H), 3.88–4.02 (m; 2H), 3.01 (d, J 5.7 Hz; 2H), 1.74–1.88 (m, 1H), 1.59–1.72 (m; 1H), 1.35 and 1.33 (2d; 18H). $^{13}$C NMR (DMSO-d$_6$, 75.43 MHz): δ177.42, 177.38, 161.20, 160.63, 160.16, 142.20, 133.48, 132.91, 132.78, 83.55, 83.14, 70.76, 70.40, 59.39, 56.44, 53.61, 42.30, 36.01, 33.28.

C$_{25}$H$_{37}$N$_3$O$_{10}$ (539.58).

c) (S,S)-2,7-Diamino-4-benzyloxycarbonyl-4-azaoctanedioic acid (S,S)-2,7-Bis(tert-butyloxycarbonylamino)-4-benzyloxycarbonyl-4-azaoctanedioic acid (0.29 g, 0.37 mmol) was dissolved in TFA (10 ml), the solution stirred at ambient temperature for 2 hours and the TFA distilled off to yield the title compound which was used in the subsequent step without further purification.

d) (S,S)-Benzyloxycarbonyl-2,7-bis(9-fluorenyl-methoxy-carbonyl)-4-azaoctanedioic acid (S,S)-2,7-Diamino-4-benzyloxycarbonyl-4-azaoctanedioic acid (0.2 g, 0.37 mmol) was dissolved in dioxane (10 ml) and H$_2$O (10 ml), 9-fluorenylmethylchloroformate (0.29 g, 1.11 mmol) and 1M NaHCO$_3$ (2.96 ml, 2.96 mmol) added with stirring at 0° C., stirring continued for 10 hours at ambient temperature and the solvents evaporated. The residual solid was triturated with chloroform (5 ml) while the pH was kept at pH 5 by addition of acetic acid. The solution was subsequently evaporated and the product isolated after chromatography on silica gel (AcOEt:hexane:AcOH 10:10:1).

Yield: 0.1 g (35%) as a white solid.

$^1$H NMR (DMSO-d$_6$, 300 MHz): δ7.21–7.44, 7.61–7.91 (m; 22H), 6.88 (d, J 6.3 Hz; 1H), 4.96 (s; 2H), 4.56 (dd, J 10.8 Hz, J 3.3 Hz; 1H), 3.94–4.28 (m; 8H), 3.08 (d, J 5.7 Hz; 2H), 1.86–1.98 (m, 1H), 1.69–1.82 (m; 1H). $^{13}$C NMR (DMSO-d$_6$, 75.43 MHz): δ172.98, 172.49, 156.49, 156.04, 144.32, 144.24, 144.17, 142.97, 141.07, 139.81, 137.82, 137.55, 129.30, 128.66, 128.06, 127.99, 127.66, 127.46, 125.68, 121.75, 120.39, 110.06, 66.22, 65.60, 55.26, 52.20, 47.08, 47.04, 36.63, 37.74.

C$_{45}$H$_{41}$N$_3$O$_{10}$ (783.83).

Solid-Phase Synthesis of Peptides

Solid-phase peptide synthesis was carried out essentially according to the principles of the fluorenylmethoxycarbonyl (Fmoc)-polyamide strategy (Atherton & Sheppard, *Solid phase peptide synthesis: a practical approach*. Oxford: IRL Press at Oxford University Press, 1989). Commercially available synthesis resins were used; for batch synthesis either manually or using a semi-automatic instrument (Labortec Peptide Synthesizer 5P 650) these were of polystyrene with acid-labile (Wang, *J. Am. Chem. Soc.*, 95, 1328–1333, 1973) or acid hyperlabile linkage agents (Merger et al., *Tetrahedron Letters* 29, 4005–4008, 1988). Alternatively, peptides were assembled in fully automatic mode on flow resins (Atherton et al., *J. Chem. Soc., Chem. Commun.*, 1151–2, 1981) using an LKB Biolynx 4170 Automated Peptide Synthesizer. Synthesis resins were purchased which already contained the protected desired C-terminal Fmoc-amino acid residue. Chain elongation was achieved variously with side-chain protected Fmoc-amino acid pentafluorophenyl esters (Kisfaludy & Schoen, *Synthesis*, 325–327, 1983), using activation with dicyclohexylcarbodiimide (DCC)/1-hydroxybenzotriazole (HOBt) (Koenig & Geiger, *Chem. Ber.* 103, 2034–2040, 1970) or using the coupling reagent PyBOP (Coste et al., *Tetrahedron Lett.*, 31, 205–208, 1990). The lysine side-chain amino group was protected with the t-butyloxycarbonyl function, the side-chain carboxyl groups of glutamic and aspartic acid were protected as the t-butyl esters.

Synthesis resin bearing the desired N-deprotected C-terminal residue was acylated with one half equivalent of Fmoc-protected diaminodicarboxylic acid with the aid of DCC and HOBt. After completion of the reaction excess reagents were washed off. The peptidyl resin was then treated once more with DCC/HOBt in order to anchor carboxyl groups which may have remained free. After this step the resin was washed with methanol to deactivate any carboxyl groups unable to be linked with resin-bound amino groups. Finally excess amino groups were capped by acetylation. The peptide synthesis was then continued as usual.

After complete solid-phase assembly of the desired sequences, the peptides were cleaved from the synthesis resins with concomitant side-chain deprotection using trifluoroacetic acid to which suitable scavenger chemicals (King et al., *Int. J. Peptide Protein Res.*, 36 255–268, 1990) had been added. After evaporation, the peptides were isolated by precipitation with diethyl ether and drying. Purification was by preparative reversed phase high performance liquid chromatography.

TABLE 1

Analytical data for peptides with the general structure (Pyr—Glu—Asp)$_2$-bridge residue-(Lys—OH)$_2$

| Bridge Residue Type[a] | HPLC Method[b] (Retention time, min) | Purity[c] (%) | FAB—MS [M+ H]$^+$ |
|---|---|---|---|
| C-6 | 10-40-20 (16) | 95 | 1199.5 |
| C-5 | 0-30-20 (17) | 95 | 1185 |

TABLE 1-continued

Analytical data for peptides with the general structure
(Pyr—Glu—Asp)$_2$-bridge residue-(Lys—OH)$_2$

| Bridge Residue Type[a] | HPLC Method[b] (Retention time, min) | Purity[c] (%) | FAB—MS [M+ H]$^+$ |
|---|---|---|---|
| C-1 | | | |
| C—O (meso) | 0-20-20 (19) | 98 | 1115.4 |
| C—O (isomer 1) | 0-20-20 (19) | 98 | 1115.4 |
| C—O (isomer 2) | 0-20-20 (19) | 97 | 1115.4 |
| C-4-trans-ene | 0-30-20 (12) | 98 | 1169.4 |
| C-4-cis-ene | 10-40-20 (13) | 100 | 1170.6 |
| C-4-yne | 0-30-20 (19) | 98 | 1167.5 |
| C-4-vic-glycol (isomer 1) | 0-30-20 (14) | 98 | 1203.2 |
| C-4-vic-glycol (isomer 2) | 0-30-20 (13) | 98 | 1203.4 |
| C-4-vic-glycol (isomer 3) | | | |
| C-3-Amine | | | |
| C-3-Ether | | | |

[a] Refer to Examples
[b] The methods are expressed as gradients of mobile phase B in A over time, eg. 10-40-20 refers to a gradient starting at 10 and finishing at 40% B over 20 minutes. Mobile phases: A) 0.1% TFA B) 0.1% TFA in 40% MeCN. Column: Vydac TP54,C18,0.46 × 25 cm, 5 μm particles, 100Å pore; flow 1 mL/min
[c] Refers to integration of HPLC chromatogram peaks (λ = 215 nm)

TABLE 2

Amino acid analysis data for peptides with the general structure
(Pyr—Glu—Asp)$_2$-bridge residue-(Lys—OH)$_2$

| Bridge Residue Type[a] | Asp found (theory) | Glu found (theory) | Lys found (theory) |
|---|---|---|---|
| C-6 | 1.0 (1) | 2.15 (2) | 0.93 (1) |
| C-5 | 1.0 (1) | 2.18 (2) | 0.94 (1) |
| C-1 | | | |
| C-0 (meso) | 1.0 (1) | 2.15 (2) | 0.93 (1) |
| C-0 (isomer 1) | 1.0 (1) | 2.18 (2) | 0.93 (1) |
| C-0 (isomer 2) | | | |
| C-4-trans-ene | 1.0 (1) | 2.15 (2) | 0.93 (1) |
| C-4-cis-ene | 1.0 (1) | 2.17 (2) | 0.93 (1) |
| C-4-yne | 1.0 (1) | 2.17 (2) | 0.95 (1) |
| C-4-vic-glycol (isomer 1) | 1.0 (1) | 2.15 (2) | 0.93 (1) |
| C-4-vic-glycol (isomer 2) | | | |
| C-4-vic-glycol (isomer 3) | | | |
| C-3-Amine | | | |
| C-3-Ether | | | |

[a] Refer to Examples

EXAMPLE 16

Peptide synthesis: (pGlu-Glu-Asp)$_2$-(E)-DHs (Lys)$_2$

The peptide was synthesized using a Labortec Peptide Synthesizer. Fmoc-Lys(Boc)-Sasrin polymer (1.0 g, 0.6 mmol; Bachem A. G.; substitution 0.6 mmol/g) was charged into a 100 ml reaction flask. Fmoc-DHs (150 mg, 0.23 mmol), DCC (290 mg, 1.4 mmol) and HOBt (211 mg, 1.4 mmol) in DMF (20 ml) were added to the polymer and the reaction allowed to proceed for 9 hours. Additional DCC (1.4 mmol) and HOBt (1.4 mmol) were added and the reaction allowed to proceed for another 2 hours. The polymer was then washed with CH$_2$Cl$_2$, with 30% MeOH in CH$_2$Cl$_2$ and with DMF. Free amino groups on the polymer were acetylated using 10% Ac$_2$O in DMF (3x over 1 hour; negative Kaiser test).

The remaining synthesis was carried out by standard protocol using Fmoc-Asp(OtBu)-Opfp (1.33 g, 2.3 mmol), Fmoc-Glu(OtBu)-Opfp (1.35 g, 2.3 mmol) and pGlu-pentachlorophenyl ester (0.86 g, 2.3 mmol). HOBt (350 mg, 2.3 mmol) was added in each coupling step which was allowed to proceed for 1 hour. Completion of the coupling was ascertained by negative Kaiser test. After the coupling with the Fmoc-amino acid the polymer was washed with DMF, the protecting group cleaved off by 20% piperidine in DMF, and the polymer again washed with DMF. After the final coupling the polymer was washed with MeOH/CH$_2$Cl$_2$ and CH$_2$Cl$_2$. The weight of dried polymer-peptide was 1 g. The peptide was cleaved from the polymer by TFA:CH$_2$Cl$_2$ 1:1, the solution freeze-dried, the residue dissolved in water, filtered (0.45μ) and the filtrate freeze-dried; yield 430 mg. For further purification 100 mg of this product was dissolved in water (0.5 ml) and subjected to preparative HPLC using 2.1×15 cm Beckman Ultrasphere ODS and solutions A 0.1% TFA in H$_2$O, B 0.1% TFA in MeCN:H$_2$O 40:60. The gradient was 0–15% B, 120 minutes, flow rate 5 ml/minute. 19 mg of pure peptide (>95%) was obtained after freeze-drying. FAB-MS: [M+H] 1169.3.

HOBt=Hydroxybenzotriazole
Pfp=Pentafluorophenyl
Fmoc=9-Fluorenylmethoxycarbonyl
Boc=t-Butoxycarbonyl
DCC=Dicyclohexylcarbodiimide
(E)-DHs =(S,S)-2,7-Diamino-(E)-oct-4-ene-1,8-dioic acid.

We claim:
1. A peptide compound of formula II

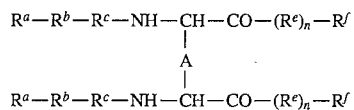

wherein —A— is a C$_{1-6}$ carbon chain interrupted by one or more double or triple carbon-carbon bonds,
$R^a$ represents

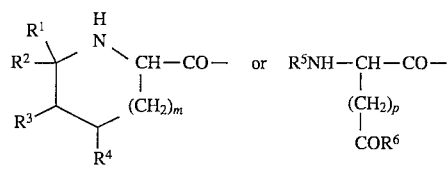

or

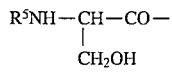

$R^b$ represents

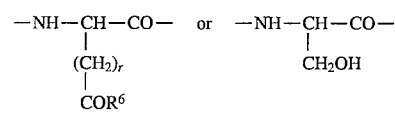

$R^c$ represents

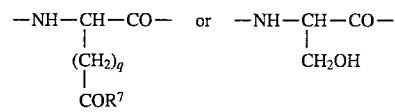

$R^e$ represents

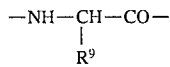

and $R^f$ represents

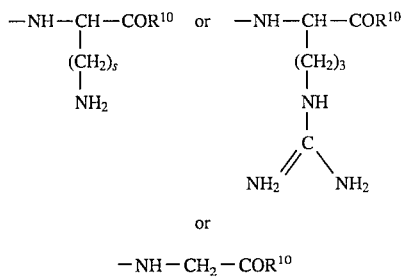

or $$-NH-CH_2-COR^{10}$$

(wherein n and m independently represent 0 or 1;

p, q and r independently represent 1 or 2;

s represents 3 or 4;

$R^1$ and $R^2$ are both hydrogen atoms or together represent an oxo group;

$R^3$ and $R^4$ are both hydrogen atoms or together represent a carbon-carbon bond;

$R^5$ is hydrogen or an acyl group;

each $R^6$ and $R^7$ independently represent a hydroxy group or an amino group, but are preferably hydroxy groups, $R^8$ represents hydrogen; a $C_{2-6}$ alkyl group; a $C_{7-20}$ aralkyl group, which may carry one or more hydroxy, amino or methoxy substituents; or a metabolically labile S-protecting group;

$R^9$ represents hydrogen or a methyl group; and $R^{10}$ represents a hydroxy or amino group, the residue of the amino acid glutamine or a peptide having an N-terminal glutamine unit).

2. A peptide compound as claimed in claim 1 wherein —A— is selected from the group consisting of:

—HC═CH—

—HC═C═CH—

—CH$_2$—CH═CH—CH$_2$

—CH$_2$C≡C—CH$_2$—

—CH$_2$—CH═CH—CH═CH—CH$_2$—

—CH$_2$—CH$_2$—C≡C—CH$_2$—CH$_2$— and

—CH$_2$—C≡C—C≡C—CH$_2$—.

3. A peptide compound as claimed in claim 2 wherein —A— is selected from the group consisting of:

(E)-buten-2-enylene, (Z)-buten-2-enylene, and buten-2-ynylene.

4. The peptide compound of claim 1 wherein n represents 0.

5. The peptide compound of claim 1 wherein m represents 0.

6. The peptide compound of claim 1 having the formula:

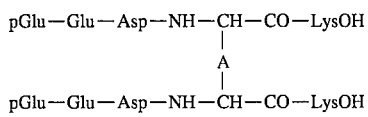

wherein —A— is as defined in claim 1.

7. A pharmaceutical composition comprising a peptide compound as claimed in claim 1 together with a pharmaceutical carrier or excipient.

8. A method of stimulating cell division in a patient, said method comprising administering to said patient an effective amount of a peptide compound as claimed in claim 1.

9. The method of claim 8 wherein division of myelopoietic or bone marrow cells is stimulated.

10. A process for producing a peptide compound as claimed in claim 1 comprising deprotecting a partially or fully protected derivative thereof.

11. (pGlu-Glu-Asp)$_2$-[L,L-2,7-diamino-cis-3,4-dehydrosuberyl]-(Lys-OH)$_2$.

* * * * *